(12) United States Patent
Frost

(10) Patent No.: US 6,472,190 B1
(45) Date of Patent: Oct. 29, 2002

(54) BIOCATALYTIC SYNTHESIS OF GALLOID ORGANICS

(75) Inventor: John W. Frost, Okemos, MI (US)

(73) Assignee: Board of Trustees operating Michigan State Univerisity, East Lansing, MI (US)

( * ) Notice: Subject to any disclaimer, the term of this patent is extended or adjusted under 35 U.S.C. 154(b) by 0 days.

(21) Appl. No.: 09/527,145

(22) Filed: Mar. 16, 2000

(51) Int. Cl.[7] .............................. C12P 7/40; C12N 1/20; C12N 15/00

(52) U.S. Cl. ................ 435/156; 435/252.33; 435/320.1

(58) Field of Search ................................. 435/136, 156, 435/252.33, 320.01

(56) References Cited

U.S. PATENT DOCUMENTS

| | | | |
|---|---|---|---|
| 4,172,960 A | | 10/1979 | Baldwin et al. |
| 5,168,056 A | * | 12/1992 | Frost ........................ 435/172.3 |
| 5,272,073 A | * | 12/1993 | Frost et al. .................. 435/155 |
| 5,629,181 A | * | 5/1997 | Frost et al. .................. 435/156 |
| 5,776,736 A | * | 7/1998 | Frost et al. ................. 435/108 |
| 5,798,236 A | * | 8/1998 | Frost et al. .................. 435/136 |

FOREIGN PATENT DOCUMENTS

| | | |
|---|---|---|
| DE | 2653446 | 6/1977 |
| JP | 75151832 | of 1975 |
| WO | WO 95/07979 | 3/1995 |

OTHER PUBLICATIONS

Deschamps A. M. et al, Production of gallic acid from tara tannin by bacterial strains, Biotechnology Letters, 1984, 6, 237–242.*
Nakajima H et al.: "Decarboxylation of gallate by cell–free extracts of *Streptococcus faecalis* and *Klebsiella pneumoniae* isolated from rat feces." Journal of the Food Hygienic Society of Japan, vol. 33, No. 4, 1992, pp. 371–377.
Frost J W et al.: "Biocatalytic syntheses of aromatics from D–glucose: renewable microbial sources of aromatic compounds" Annual Review of Microbiology, vol. 49, 1995, pp. 557–579.
Frost J W: "Biocatalytic synthesis of galloid organics from glucose;" Abstr. Pap. Am. Chem. Soc. 209th ACS National Meeting Anaheim, CA, vol. 209, No. 2, Apr. 2, 1995, p. 132–BTEC.
Osawa R et al.: "Metabolism of tannin–protein complex by facultatively anaerobic bacteria isolated from koala feces." Biodegradation, vol. 4, No. 2, 1993, pp. 91–99.
Werner I et al.: "Retrobiosynthetic NMR studies with 13C–labeled glucose. Formation of gallic acid in plants and fungi." Journal of Biological Chemistry, vol. 272, No. 41, 1997, pp. 25474–25482.

Richman J E et al.: "Reaction of 3–dehydroshikimic acid with molecular oxygen and hydrogen peroxide: Products, mechanism, and associated antioxidant activity." Journal of the American Chemical Society, vol. 118, No. 46, 1996, pp. 11587–11591.
Frost J: "Renewable feedstocks." Chem. Eng. (Rugby, Engl.); vol. 611, May 16, 1996, pp. 32–35.
Kamborakis S et al.: "Synthesis of Gallic Acid and Pyrogallol from Glucose: Replacing Natural Product Isolation with Microbial Catalysis," Journal of American Chemistry Society, vol. 122, 2000, pp. 9042–9043.
Draths, K.M. et al., Benign by Design; "Microbial Biocatalysis," Anasta, P.T.; Farris C.S. Ed.; ACS Symposium Series 577; American Chemical Society: Washington, D.C., Chap. 3, p. 32 (1994).
Draths, K.M. et al., "Environmentally Compatible Synthesis of Adipic Acid from D–Glucose," J. Am. Chem. Soc. 116:399 (1994).
Draths, K.M. et al., "Environmentally Compatible Synthesis of Catechol from D–Glucose," J. Am. Chem. Soc. 117:2395 (1995).
Entsch, B. et al., "Catalytic Function of Tyrosine Residues in para–Hydroxybenzoate Hydroxylase as Determined by the Study of Site–directed Mutants," J. Biol. Chem. 266:17341 (1991).
Eschrich, K. et al., "Role of Tyr201 and Tyr 385 in substrate activation by p–hydroxybenzoate hydroxylase from *Pseudomonas fluorescens*," Eur. J. Biochem. 216:137 (1993).
Frost, J.W. et al., "Dehydroquinate Synthase from *Escherichia coli*: Purification, Cloning, and Construction of Overproducers of the Enzyme," Biochemistry 23:4470 (1984).
Haslam, E. et al., "The Biosynthesis of Gallic Acid," J. Chem. Soc. 1854 (1961).
Kawakubo, J. et al., "Isolation of a Gallic Acid–producing Microorganism with Sake Cake Mediuim and Production of Gallic Acid," Biosci. Biotech. Biochem. 57:1360 (1993).
Korth, H., "Bildung von Gallussäure–haltigen Nährmedium durch *Enterobacter cloacae* und *Pseudomonas fluorescens*," Arch. Mikrobiol. 89:67 (1973).
Li, K. et al., "Fed–Batch Fermentor Synthesis of 3–Dehydroshikimic Acid Using Rcombinant *Escherichia coli*," Biotechnol. Bioeng. 64:61 (1999).
Li, K. et al., "Synthesis of Vanillin from Glucose," J. Am. Chem. Soc. 120:10545 (1998).

(List continued on next page.)

Primary Examiner—Ponnathapu Achutamurthy
Assistant Examiner—Malgorzata A. Walicka
(74) Attorney, Agent, or Firm—Harness, Dickey & Pierce, P.L.C.

(57) ABSTRACT

The present invention provides a bioengineered synthesis scheme for the production of gallic acid from a carbon source. Methods of producing gallic acid from a carbon source based on the synthesis scheme are also provided. The gallic acid produces from these methods can be further converted to pyrogallol. Methods for the biosynthesis of pyrogallol from gallic acid are also provided.

22 Claims, 5 Drawing Sheets

OTHER PUBLICATIONS

Nichols, N.N. et al., "Repression of 4–Hydroxybenzoate Transport and Degradation by Benzoate: a New Layer of Regulatory Control in the *Pseudomonas putida* β–Ketoadipate Pathway," J. Bacteriol. 177:7033 (1995).

Nichols, N.N. et al., "PcaK, a High–Affinity Permease for the Aromatic Compounds 4–Hydroxybenzoate and Protocatechuate from *Pseudomonas putida*," J. Bacteriol. 179:5056 (1997).

Ogino, T. et al., "Biosynthesis of aromatic compounds: 13C NMR spectroscopy of whole *Escherichia coli* cells," PNAS (USA) 79:5828 (1982).

Rivero, F. et al., "Spore germination in Phycomyces blakesleeanus," Mycologia 86:781 (1994).

Snell, K. et al., "Synthetic Modification of the *Escherichia coli* Chromosome: Enhancing the Biocatalytic Conversion of Glucose into Aromatic Chemicals," J. Am. Chem. Soc. 118:5605 (1996).

Weaver, L.M. et al., "Cloning of an aroF Allele Encoding a Tyrosine–Insensitive 3–Deoxy–D–arabino–Heptulosonate 7–Phosphate Synthase," J. Bacteriol. 172:6581 (1990).

Zeida, M. et al., "Purification and Characterization of Gallic Acid Decarboxylase from *Pantoea agglomerans* T71," Appl. Environ. Micriobiol. 64:4743 (1998).

* cited by examiner

Biocatalytic synthesis of PGL and catechol from glucose

FED-BATCH, AEROBIC CULTIVATION OF *E. coli* KL7/pSK6.161:
▲ CELL GROWTH, ☐ GALLIC ACID (GA); ⊠ PROTOCATECHUIC ACID (PCA);
▨ 3-DEHYDROSHIKIMIC ACID (DHS); ■ 3-DEOXY-D-*ARBINO*-HEPTULOSONIC
ACID (DAH); ▨ GLUTAMIC ACID (GLU)

Conversion of DHS into GA using KL7/pSK6.76; DHS is all added in one portion at 11 h. (□) GA, (▨) PCA, (▧) DHS, (▲) Cell g dry wt/L.

Conversion of DHS into GA using KL7/pSK6.76; DHS is added with the glucose feed. (□) GA, (▨) PCA, (▧) DHS, (▲) Cell g dry wt/L.

Conversion of PCA into GA using KL7/pSK6.118; PCA added all in one portion at 10 h ; (□) GA, (▨) PCA, (▧) DHS, (▲) Cell g dry wt/L.

Conversion of PCA into GA using KL7/pSK6.118; PCA addition with the glucose feed. (□) GA, (▨) PCA, (▧) DHS, (▲) Cell g dry wt/L.

Anaerobic decarboxylations catalyzed by
RB791serA::aroB/pSK6.234: ☐ gallic acid (GA),
■ pyrogallol, ▨ protocatechuic acid (PCA), ▨ catechol.

*Klebsiella oxytoca* M5a1. Decarboxylation of GA to PGL using bacteria cultured under fed-batch fermentor conditions. Time is measured from the addition of gallic acid. Gallic acid ( ☐ ), pyrogallol ( ▤ ) and total GA and PGL concentration ( ▲ ).

US 6,472,190 B1

BIOCATALYTIC SYNTHESIS OF GALLOID ORGANICS

SPONSORSHIP

Work on this invention was sponsored in part by the National Science Foundation Grant No. CHE9633368 and the Environmental Protection Agency Grant No. CR822940. The Government may have certain rights in the invention.

FIELD OF THE INVENTION

The present invention is related to the production of galloid organics and more specifically to methods of producing gallic acid and pyrogallol from bioconversion of a carbon source.

BACKGROUND OF THE INVENTION

Among a spectrum of uses, gallic acid and pyrogallol are often incorporated into chemical syntheses to provide the trihydroxylated aromatic ring of biologically-active molecules such as the antibiotic trimethoprim 1, the coronary vasodilator trimetazidine 2, the insecticide bendiocarb 3, and the muscle relaxant gallamine triethiodide 4. The current commercial sources

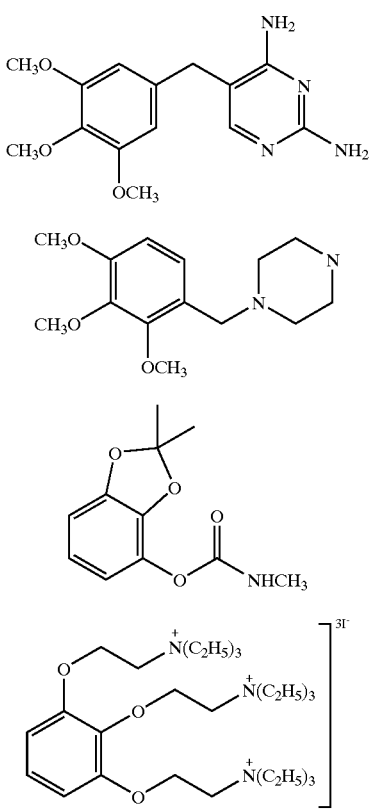

of gallic acid include gall nuts, an insect carapace harvested in China, and tara powder, an isolate derived from the ground seed pod of a tree found in Peru (Leston, G. In *Kirk-Othmer Encyclopedia of Chemical Technology*; Kroschwitz, J. I.; Howe-Grant, M., Ed.; Wiley: New York (1996), Vol. 19, p. 778). Pyrogallol is currently synthesized by thermal decarboxylation of gallic acid in copper autoclaves (Leston, G. In *Kirk-Othmer Encyclopedia of Chemical Technology*; Kroschwitz, J. I.; Howe-Grant, M., Ed.; Wiley: New York (1996), Vol. 19, p. 778).

Because of the continuing uncertainties of supplies of gall nuts and tara powder, which are used for gallic acid and pyrogallol manufacture, there is interest in the development of synthetic processes. Various approaches were investigated in the synthesis of pyrogallol from readily available petrochemicals. The first synthetic pyrogallol that was industrially manufactured used basic hydrolysis of 2,2,6,6-tetrachlorocyclohexanone (German Patent No. 2,653,446). The preparation of the starting material by chlorination of cyclohexanone in the presence of collidine as the catalyst has been patented (British Patent No. 1,258,700). Cyclohexanone's main commercial synthesis begins with benzene, a petroleum-derived chemical with known toxic and carcinogenic activity. Other synthetic approaches involve hydroxylation of resorcinol with 50% $H_2O_2$ in the presence of hexafluoroacetone at 60° C. to give a mixture of pyrogallol and 1,2,4-trihydroxybenzene (Japan Patent No. 75151832), or hydrolysis of 2,6-dimethoxyphenol using 48% hydrobromic acid (U.S. Pat. No. 4,172,960). The 2,6-dimethoxyphenol is produced by reaction of 2,6-dibromophenol with sodium methoxide.

Therefore, it would be desirable to provide methods for obtaining large quantities of gallic acid and pyrogallol that did not require the isolation of natural products from non-row crops. It would also be desirable if the methods were cost-efficient using inexpensive starting materials. Furthermore, such methods should be simple and environmentally benign.

SUMMARY OF THE INVENTION

A bioengineered synthesis scheme for production of gallic acid from a carbon source is provided. In one embodiment, the bioconversion methods of the present invention comprise the microbe-catalyzed conversion of a carbon source to gallic acid. As shown in the synthesis scheme of FIG. 1, the microbe-catalyzed conversion of the present invention requires five enzymes which may be provided by a recombinant microbe. In a preferred embodiment, the recombinant microbe is *Escherichia coli* designed to cause the two-step conversion of 3-dehydroshikimic acid to gallic acid.

A bioengineered scheme for the production of pyrogallol from gallic acid is also provided. In one embodiment, the bioconversion methods of the present invention comprise the microbe-catalyzed conversion of gallic acid to pyrogallol. As shown in the synthesis scheme of FIG. 1, the microbe-catalyzed conversion step requires one enzyme which may be provided by a recombinant microbe. In a preferred embodiment, the recombinant microbe is *Escherichia coli* designed to cause the decarboxylation of gallic acid to pyrogallol.

The biocatalytic synthesis methods for gallic acid and pyrogallol provided herein are believed to be environmentally benign, economically attractive, and utilize abundant renewable sources as a starting materials.

Additional objects, advantages, and features of the present invention will become apparent from the following description and appended claims, taken in conjunction with the accompanying drawings.

BRIEF DESCRIPTION OF THE DRAWINGS

The various advantages of the present invention will become apparent to one skilled in the art by reading the following specification and subjoined claims and by referencing the following drawings in which:

DETAILED DESCRIPTION OF THE PREFERRED EMBODIMENTS

A bioengineered synthesis scheme for the production of gallic acid from a carbon source is provided herein. Methods of producing gallic acid from a carbon source based on the synthesis scheme are also provided. A bioengineered synthesis scheme for the production of pyrogallol from a carbon source is also provided herein. Methods of producing pyrogallol from a carbon source based on the synthesis scheme are provided. In one embodiment, a method is provided wherein the carbon source is converted to gallic acid by a first recombinant microbe and the gallic acid further converted to pyrogallol by a second microbe.

Gallic acid has been detected in cultures of *Phycomyces blakesleeanus* (Haslam, E. et al., *J. Chem. Soc.* 1854 (1961); Rivero, F. et al., *Mycologia* 86:781 (1994)), *Pseudomonas fluorescens* (Korth, H., Arch. Mikrobiol. 89:67 (1973), *Entorobacter cloacae* (Korth, H., *Arch. Mikrobiol.* 89:67 (1973), *Aspergillus terreus* (Kawakubo, J. et al., *Biosci. Biotech. Biochem.* 57:1360 (1993), and recombinant *E. coli* (Li, K. et al., *Biotechnol. Bioeng.* 64:61 (1999)). However, the pathway for forming gallic acid in these microbes have not been elucidated. The biosynthetic scheme of the present invention (FIG. 1) is novel in that it utilizes enzymes that are not involved in gallic acid synthesis in nature. For example, neither 3-dehydroshikimate dehydrogenase or protocatechuic hydroxylase activities have been detected in the microbes which are thought to produce gallic acid.

Figure 1:
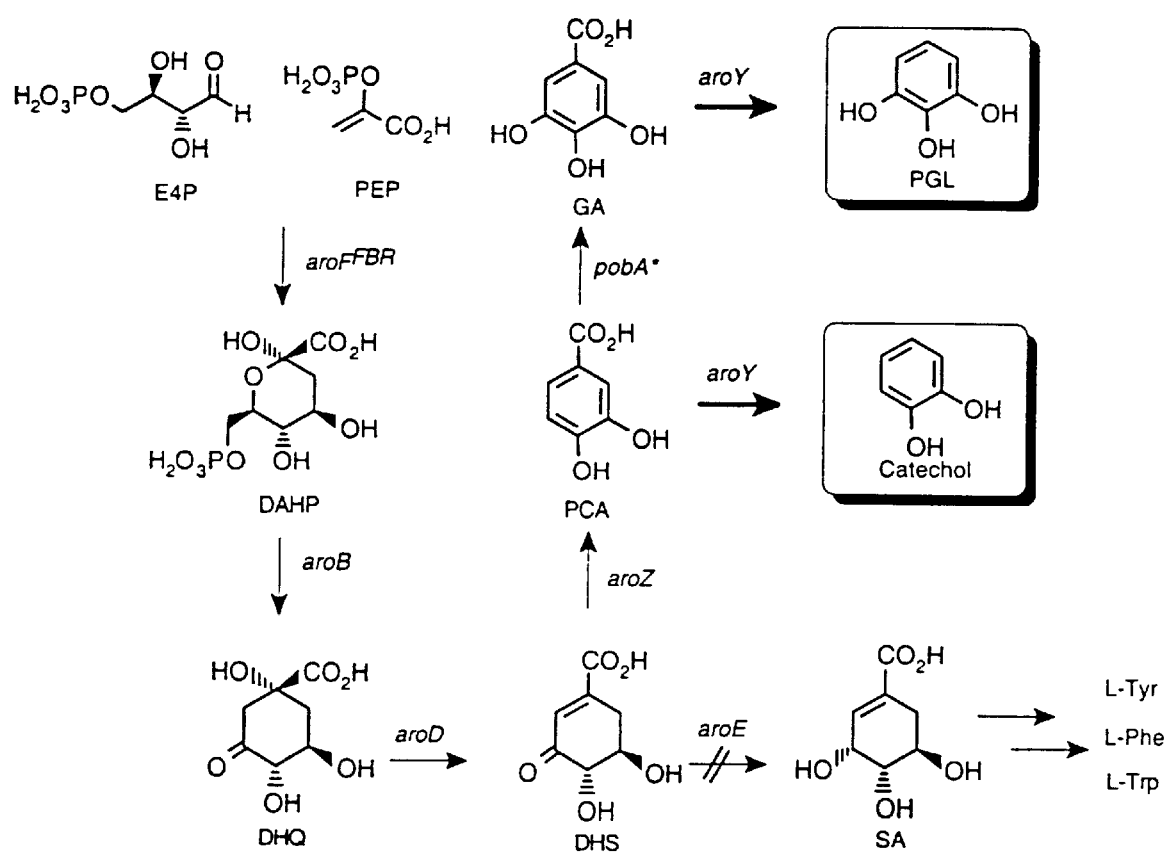
FIG. 1 is a schematic illustrating the bioengineered synthesis scheme of the present invention for producing gallic acid and pyrogallol.

In one embodiment, a method is provided wherein the carbon source is converted to gallic acid by a recombinant microbe. Manipulation of the common aromatic amino acid biosynthetic pathway of the microbe results in a significant production of gallic acid when the recombinant microbe is cultured in the presence of a carbon source. The carbon source is converted to 3-deoxy-D-arabino-heptulosonate-7-phosphate (DAHP) which is subsequently converted by 3-dehydroquinate synthase to 3-dehydroquinate (DHQ) which is then dehydrated to 3-dehydroshikimic acid (DHS) by 3-dehydroquinate dehydratase (FIG. 1). 3-dehydroshikimic acid is dehydrated to protocatechuic acid (PCA) by 3-dehydroshikimate dehydratase which is then converted by a mutant p-hydroxybenzoate hydroxylase to gallic acid (GA) (FIG. 1). The recombinant microbe comprises the genes encoding for the enzymes necessary to convert the carbon source to gallic acid.

In an alternative embodiment, a method is provided for the conversion of 3-dehydroshimic acid to gallic acid by a recombinant microbe. The 3-dehydroshikimic acid is converted to protocatechuic acid by 3-dehydroshikimate dehydratase which is then hydrodroxylated to gallic acid by a mutant p-hydroxybenzoate hydroxylase. In a further embodiment, a method is provided for the conversion of the protocatechuic acid to gallic acid by a different recombinant microbe. The protocatechuic acid is converted to gallic acid by a mutant p-hydroxybenzoate hydroxylase.

In yet another embodiment, a method is provided wherein the gallic acid is converted to pyrogallol by a second microbe. In a preferred embodiment, pyrogallol is produced from gallic acid by a recombinant microbe. The gallic acid is converted to pyrogallol by protocatechuic acid decarboxylase (FIG. 1).

The bioconversion methods of the present invention are carried out under conditions of time, temperature, pH, nutrient type and concentration, aeration conditions and glucose concentrations to provide maximal conversion of the carbon source to gallic acid and pyrogallol. As described in detail in the Specific Examples, in a preferred embodiment, a fed-batch fermentor is used to convert the carbon source to gallic acid and then pyrogallol, followed by isolation of either the gallic acid or pyrogallol from the fermentation broth by extraction with an organic solvent. The batch fermentor process and extraction methods are known to those skilled in the art.

As used herein, the phrase "carbon source" is meant to include biomass derived carbon sources, including but not limited to, polymeric and/or monomeric xylose, arabinose, and glucose, as well as glycerol, and the intermediates of the Krebs cycle (e.g., dicarboxylic acids), either alone or in combination. In a preferred embodiment, the carbon source is glucose. The carbon source may be derived from renewable resources such as, without limitation, corn, sugar beets and sugar cane.

Enhanced expression of genes coding for proteins able to perform or control the induction of this divergent pathway or common aromatic pathway enzymatic functions is mediated by genetic elements transferable into a host cell. Genetic elements as herein defined include nucleic acids (generally DNA or RNA) having expressible coding sequences for products such as proteins, apoproteins, or antisense RNA, which can perform or control pathway enzymatic functions. The expressed proteins can function as enzymes, repress or derepress enzyme activity, or control expression of enzymes. The nucleic acids coding these expressible sequences can be either chromosomal (e.g., integrated into a host cell chromosome by homologous recombination) or extrachromosomal (e.g., carried by plasmids, cosmids, etc.). In addition, genetic elements are defined to include optional expression control sequences including promoters, repressors, and enhancers that act to control expression or derepression of coding sequences for proteins, apoproteins, or antisense RNA. For example, such control sequences can be inserted into wild-type host cells to promote overexpression of selected enzymes already encoded in the host cell genome, or alternatively can be used to control synthesis of extrachromosomally encoded enzymes.

The genetic elements of the present invention can be introduced into a host cell by plasmids, cosmids, phages, yeast artificial chromosomes or other vectors that mediate transfer of the genetic elements into a host cell. These vectors can include an origin of replication along with cis-acting control elements that control replication of the vector and the genetic elements carried by the vector. Selectable markers can be present on the vector to aid in the identification of host cells into which the genetic elements have been introduced. For example, selectable markers can be genes that confer resistance to particular antibiotics such as tetracycline, ampicillin, chloramphenicol, kanamycin, or neomycin.

A preferred means for introducing genetic elements into a host cell utilizes an extrachromosomal multi-copy plasmid vector into which genetic elements, in accordance with the present invention, are inserted. Plasmid borne introduction of the genetic element into host cells involves an initial cleaving of a plasmid with a restriction enzyme, followed by ligation of the plasmid and genetic elements, in accordance with the invention. Upon recircularization of the ligated recombinant plasmid, transduction or other mechanism for plasmid transfer is utilized to transfer the plasmid into the host cell.

Suitable host cells for use in the present invention are members of those genera capable of being utilized for industrial biosynthetic production of desired aromatic compounds. Accordingly, host cells can include microbes which are capable of converting a carbon source to 3-dehydroshikimic acid. Non-limiting examples are *Escherichia coli,* Klebsiella, Neurospora, Nocardia and Saccharomyces. In a preferred embodiment the host cell is *E. coli.*

In one embodiment, the recombinant microbe *E. coli* is employed in the methods of the present invention. In a preferred embodiment, the *E. coli* comprises a mutated aroE locus and an aroB/aroZ cassette inserted into the serA locus. This recombinant *E. coli,* designated KL7, may further comprise a plasmid carrying an aroF$^{FBR}$ insert, a serA insert, a $P_{tac}$pobA* insert. The lack of aroE-encoded shikimate dehydrogenase results in increased synthesis of 3-dehydroshikimic acid. It will be appreciated, however, that the aroE locus mutation is not essential and is employed to ensure sufficient 3-dehydroshikimic acid formation. The 3-dehydroshikimic acid is converted into protocatechuic acid by genome-localized, aroZ-encoded 3-dehydroshikimate dehydratase. Plasmid-localized Pt$_{tac}$pobA* encodes a mutant p-hydroxybenzoate hydroxylase for conversion of protocatechuic acid into gallic acid. In addition, the second copy of aroB inserted into the genome increases 3-dehydroquinate synthase activity to the point where the enzyme no longer impedes carbon flow. Snell, K. et al., *J. Am. Chem. Soc.* 118:5605 (1996).

Figure 2:
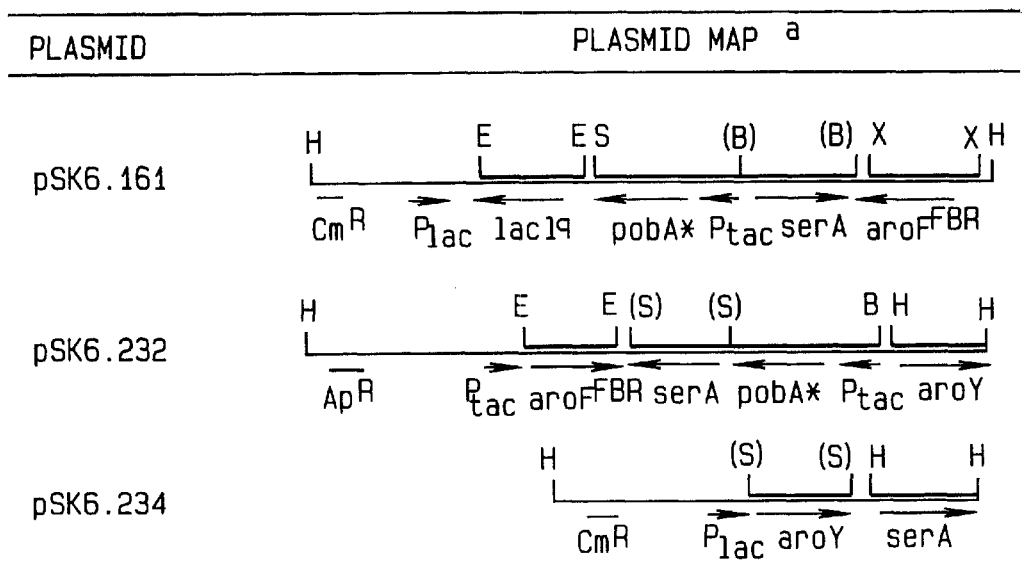
FIG. 2 is a schematic illustrating the restriction enzyme maps of plasmids pSK6.161, pSK6.232 and pSK6.234.

In a preferred embodiment, the recombinant *E. coli* comprises plasmid pSK6.161 carrying a $P_{tac}$pobA* insert, an aroF$^{FBR}$ insert, a serA insert and a lacI$^q$ insert (FIG. 2). The $P_{tac}$pobA* insert encodes for a mutant isozyme of p-hydroxy-benzoate hydroxylase able to convert protocatechuic acid to gallic acid. In this isozyme phenylalanine is substituted for tyrosine at amino acid position 385, enabling the hydroxylase to use protocatechuic acid as a substrate (Entsch, B. et al., *J. Biol. Chem.* 266:17341 (1991); Eschrich, K. et al., *Eur. J. Biochem.* 216:137 (1993)). In a preferred embodiment, the pobA* gene is from *Pseudomonas aeruginosa.* It will be appreciated by those skilled in the art however, that a gene encoding a hydroxylase able to convert protocatechuic acid to gallic acid may be used. The aroF$^{FBR}$ insert encodes a 3-deoxy-D-arabino-heptulosonic acid-7-phosphate synthase isozyme insensitive to feedback inhibition which increase carbon flow into the common pathway. Due to a mutation in the *E. coli* genomic sera locus required for L-serine biosynthesis, growth in minimal salts medium and plasmid maintenance follows from expression of plasmid-localized serA. The plasmid-localized serA insert thus allows microbial growth in minimal salts medium, distinguishing the microbes containing the plasmid from non-plasmid containing microbes.

In another embodiment, the recombinant microbe comprises regulatory elements that control the expression of the pobA*-encoded p-hydroxybenzoate hydroxylase (or any hydroxylase able to convert protocatechuic acid to gallic acid) and subsequently the conversion of protocatechuic acid to gallic acid. Gallic acid is known to be toxic to cells in high concentrations, particularly when the cells are rapidly dividing such as in early- and mid-log phases. Gallic is much less toxic to cells in late-log and stationary phase. Preferably, the expression of the pobA* gene will be repressed until late-log or stationary phase of the cells. In a preferred embodiment, the expression of the mutant p-hydroxybenzoate hydroxylase will be controlled by a combination of the lacI$^q$-encoded lac repressor and a $P_{tac}$ promoter. Expression of the mutant p-hydroxybenzoate hydroxylase can be controlled by the concentration of isopropyl-β-D-thiogalactopyranoside in the culture medium. The use of such regulatory elements is well known to those skilled in the art.

The following table sets forth the five enzymes required for the conversion of glucose to gallic acid, the genes encoding same, and the origin of the genes in the exemplary recombinant microbes of the present invention.

TABLE 1

| Enzyme† | Gene (origin) |
| --- | --- |
| a) 3-deoxy-D-arabino-heptulosonic acid 7-phosphate synthase | aroF$^{FBR}$ (plasmid) |
| b) 3-dehydroquinate synthase | aroB (additional copy inserted into genome) |
| c) 3-dehydroquinate dehydratase | aroD (genomic) |
| d) 3-dehydroshikimate dehydratase | aroZ (inserted into genome) |
| e) p-hydroxybenzoate hydroxylase | $P_{tac}$ pobA* (plasmid) |

†Enzymes a)–e) correspond to a–e of FIG. 1.

In an alternative embodiment, 3-dehydroshikimic acid is converted to gallic acid by a recombinant microbe. The recombinant microbe comprises genes encoding for 3-dehydroshikimate dehydratase and the mutant isozyme of p-dehydroxybenzoate hydroxylase. The conversion of 3-dehydroshikmic acid to protocatechuic acid is catalyzed by 3-dehydroshikimate dehydratase and the subsequent conversion of protocatechuic acid to gallic acid is catalyzed by the p-hydroxybenzoate hydroxylase. In a preferred embodiment, the recombinant microbe is *E coli* comprising plasmid carrying a $P_{tac}$pobA* insert, and an aroZ insert. In a more preferred embodiment, the recombinant *E. coli* is KL7 further comprising the plasmid pSK6.76 carrying an aroZ insert, a $P_{tac}$pobA* insert and a serA insert. The aroZ insert encodes for a 3-dehydroshikmate dehydratase. The $P_{tac}$pobA* insert encodes for an isozyme of p-hydroxybenzoate hydroxylase able to hydroxylate protocatechuic acid to gallic acid.

In yet another embodiment, protocatechuic acid is converted to gallic acid by a recombinant microbe. The recombinant microbe comprises a gene encoding for the mutant isozyme of p-hydroxybenzoate hydroxylase able to hydroxylate protocatechuic acid to gallic acid. In a preferred embodiment, the recombinant microbe is *E. coli* comprising a plasmid carrying a $P_{tac}$pobA* insert. In a more preferred embodiment, the recombinant *E. coli* is KL7 further comprising the plasmid pSK6.118 carrying a lacI$^q$ insert, a $P_{tac}$pobA* insert and a serA insert.

The 3-dehydroshikimic acid and protocatechuic acid can be obtained from various sources. Preferably, 3-dehydroxshikimic acid is obtained by the conversion of glucose by a recombinant microbe. For example, culturing of recombinant *E. coli* KL3/pKL4.79B converts glucose to 3-dehydroshikimic acid (Li, K. et al., *Biotechnol. Bioeng.* 64:61 (1999)).

In another embodiment, gallic acid is converted to pyrogallol by a recombinant microbe. In a preferred embodiment, a recombinant *E. coli* microbe is employed in the methods of the present invention. In a more preferred embodiment the recombinant *E. coli* is RB791serA::aroB, which comprises an aroB cassette inserted into the serA locus and a plasmid carrying aroY and serA gene inserts. The gallic acid is converted to pyrogallol by plasmid-localized, aroy-encoded protocatechate decarboxylase. In a preferred embodiment, the aroY gene is from *Klebsiella pneumoniae*. The second copy of aroB increases 3-dehydroquinate synthase activity to the point where the enzyme no longer impedes carbon flow.

In a preferred embodiment, the recombinant *E. coli* comprises plasmid pSK6.234 carrying an aroY insert and a serA insert. As described above, the aroY gene insert encodes procatechuate decarboxylase. Although the normal substrate for protocatechuate decarboxylase is protocatechuic acid, it was discovered that it also catalyzes the decarboxylation of gallic acid to pyrogallol. Due to a mutation in the *E. coli* genomic serA locus required for L-serine biosynthesis, growth in minimal salts medium and plasmid maintenance follows from expression of plasmid-localized serA. The serA insert thus allows microbial growth in minimal salts medium, distinguishing the microbes containing the plasmid from non-plasmid containing microbes.

In an alternate embodiment, gallic acid is converted to pyrogallol by Klebsiella bacteria. Both *K. pneumoniae* and *K. oxytoca* express protocatechuic decarboxylase and can catalyze the conversion. Addition of gallic acid to the fermentation broth of a *K. oxytoca* culture resulted in a 95% conversion to pyrogallol in 12 hours.

In another embodiment, gallic acid is converted to pyrogallol by a microbe under fed-batch fermentation conditions in which the gallic acid is added to the fermentation broth when the microbe is in stationary phase. Protocatechuic decarboxylase is a cytosolic enzyme and it was not previously known if gallic acid in the fermentation medium could be taken up by the cells to produce pyrogallol. Cells cultured in shake flasks did not convert gallic acid to pyrogallol, suggesting that gallic acid is not taken up by the cells under those conditions. Addition of gallic acid to the culture medium after the cells were cultured to stationary phase in a fed-batch fermentor resulted in a 97% conversion to pyrogallol within 14 hrs. Therefore, the microbes of the present invention have the ability to convert gallic acid to pyrogallol. It is further known that gallic acid, pyrogallol and especially catechol (the product from decarboxylation or any protocatechuic acid contaminant) can be toxic to growing cells, but are less toxic when the cells are in late log or stationary phase. Therefore, addition of gallic acid to cells cultured to stationary phase will give the best yield of pyrogallol.

In a further embodiment, the conversion of gallic acid to pyrogallol is under anaerobic conditions. It was found that formation of pyrogallol was sensitive to air, decreasing the final yield of product obtained. In a preferred embodiment, the fermentation broth is sparged with a continuous flow of nitrogen upon addition of gallic acid.

In yet another embodiment, the gallic acid is produced from a carbon source by a recombinant microbe and then to pyrogallol by a second microbe. The gallic acid can be in the fermentation broth of the first microbe or purified from the broth.

Examples of the above-described preferred recombinant microbes of the present invention, *E. coli* KL7/pSK6.161, RB791serA::aroB/pSK6.234, KL7/pSK6.76 and KL7/pSK6.118 are described in Specific Examples 1–4 and have been deposited with the American Type Culture Collection (ATCC), 10801 University Boulevard, Manassas, Va. 20110-2209, under the terms of the Budapest Treaty, and accorded the ATCC designation numbers PTA-1514, PTA-1594, PTA-1513, and PTA-1512, respectively. The deposit will be maintained in the ATCC depository, which is a public depository, for a period of 30 years, or 5 years after the most recent request, or for the effective life of a patent, whichever is longer, and will be replaced if the deposit becomes depleted or nonviable during that period. Samples of the deposit will become available to the public and all restrictions imposed on access to the deposit will be removed upon grant of a patent on this application.

It will be appreciated that the pobA* gene, aroF$^{FBR}$ gene, aroY gene, serA gene and the genes encoding 3-dehydroshikimate dehydratase, protocatechuic decarboxylase and/or a hydrolase for converting protocatechuic acid to gallic, can be inserted directly into the *E. coli* genome. Such a recombinant *E. coli* would not require a plasmid to produce significant amounts of gallic acid or pyrogallol.

Although *E. coli* is specifically described herein as the microbe for carrying out the methods of the present invention, it will be appreciated that any microorganism such as the common types cited in the literature and known to those skilled in the art, may be employed, provided the microorganism can be altered to effect the desired conversion (e.g., carbon source to gallic acid, carbon source to 3-dehydroshikimate, carbon source to protocatechuic acid, 3-dehydroshikimate to gallic acid, protocatechuic acid to gallic acid, etc.) Thus, it is envisaged that many types of fungi, bacteria and yeasts will work in the methods of the present invention. Such microorganisms may be developed, for example, through selection, mutation, and/or genetic transformation processes with the characteristic and necessary capability of converting one constituent of the synthesis scheme of the present invention to another. Methods for such development are well known to the skilled practitioner.

In order to carry out the bioconversion methods of the present invention, a solution containing a carbon source is contacted with the recombinant microbe to form a bioconversion mixture which is maintained under appropriate conditions to promote the conversion of the carbon source to the desired constituent, e.g., gallic acid. In a preferred embodiment, the bioconversion mixture is maintained at a temperature of about 30° C. to about 37° C. and a pH of about 6.5 to about 7.5. It is preferred that the bioconversion mixture also contain other substances necessary to promote the viability of the recombinant microbes such as mineral salts, buffers, cofactors, nutrient substances and the like. The more general requirements for the maintenance of viability of microorganisms are well known and specific requirements for maintaining the viability of specific microorganisms are also well known as documented in the literature, or are otherwise easily determined by those skilled in the art. The gallic acid or pyrogallol may then be recovered from the bioconversion mixture by methods known in the art (e.g., organic extraction).

The foregoing and other aspects of the invention may be better understood in connection with the following examples, which are presented for purposes of illustration and not by way of limitation.

SPECIFIC EXAMPLE 1

Biocatalytic Synthesis Of Gallic Acid From Glucose

I. Results

Biosynthesis of gallic acid has been narrowed to two possible routes (FIG. 1). Leston, G., In *Kirk-Othmer Encyclopedia of Chemical Technology;* Kroschwitz, J. I.; How-Grant, M., Ed; Wiley: New York, 1996, Vol. 19, p. 778. Oxidation of 3-dehydroshikimic acid (DHS) by a dehydrogenase followed by spontaneous tautomerization could directly yield gallic acid. Alternatively, dehydration of DHS followed by hydroxylation (FIG. 1) of the resulting protocatechuic acid (PCA) could lead to gallic acid. Gallic acid has been detected in cultures of *Phycomyces blakesleeanus* (Haslam, E. et al., *J. Chem. Soc.* 1854 (1961); Rivero, F. et al., *Mycologia* 86:781 (1994)), *Pseudomonas fluorescens* (Korth, H., Arch. Mikrobiol. 89:67 (1973), *Entorobacter cloacae* (Korth, H., Arch. Mikrobiol. 89:67 (1973), *Aspergillus terreus* (Kawakubo, J. et al., *Biosci. Biotech. Biochem.* 57:1360 (1993), and recombinant *E. coli* (Li, K. et al., *Biotechnol. Bioeng.* 64:61 (1999)). However, neither DHS dehydrogenase or PCA hydroxylase activities have been detected in these microbes. DHS dehydratase activity unrelated to gallic acid biosynthesis can be detected in *Klebsiella pneumoniae* and the encoding aroZ locus has been cloned. Draths, K. M. et al., *J. Am. Chem. Soc.* 116:399 (1994); Draths, K. M. et al., *In Benign by Design;* Anasta, P. T.; Farris C. S. Ed.; ACS Symposium Series 577; American Chemical Society: Washington, D.C., Chap. 3, p. 32 (1994); Draths, K. M. et al., *J. Am. Chem. Soc.* 117:2395 (1995). Although native PCA hydroxylase activity has not been reported, mutagenesis of the *Pseudomonas aeruginosa* pobA locus encoding p-hydroxybenzoate hydroxylase produces a mutant isozyme that hydroxylates PCA to form gallic acid. Entsch, B. et al., *J. Biol. Chem.* 266:17341 (1991); Eschrich, K. et al., *J. Biochem.* 216:137 (1993).

The genome of *E. coli* KL7 contained a mutation in the aroE locus and an aroBaroZ cassette site-specifically inserted to disrupt the serA locus. Plasmid pSK6.161 carried serA, $P_{tac}$pobA*, lacI$^q$, and aroF$^{FBR}$ inserts. DHS accumulated in KL7/pSK6.161 due to the absence of aroE-encoded shikimate dehydrogenase activity. The genome-localized cassette provided the aroZ-encoded dehydratase activity for conversion of DHS into PCA. DHS synthesis, in turn, was determined by the catalytic activity of 3-deoxy-D-arabino-heptulosonic acid-7-phsophate (DHAP) synthase. Since feedback inhibition is the most important determinant of this enzyme's catalytic activity (Ogino, T. et al., *PNAS (USA)* 79:5828 (1982)), a feedback-insensitive isozyme encoded by aroF$^{FBR}$ under the control of its native promoter was utilized (Weaver, L. M. et al., *J. Bacteriol.* 172:6581 (1990)). The combination of lacI$^q$-encoded lac repressor andpobA* expressed from a $P_{tac}$ promoter enabled p-hydroxybenzoate hydroxylase activity and the conversion of PCA into gallic acid to be controlled by the concentration of isopropyl-β-D-thiogalactopyranoside (IPTG) added to the culture medium (Li, K., et al., *Biotechnol. Bioeng.* 64:61 (1999)). The serA insert ensured plasmid maintenance when KL7/pSK6.161 was cultured in medium lacking L-serine supplementation.

Figure 3:
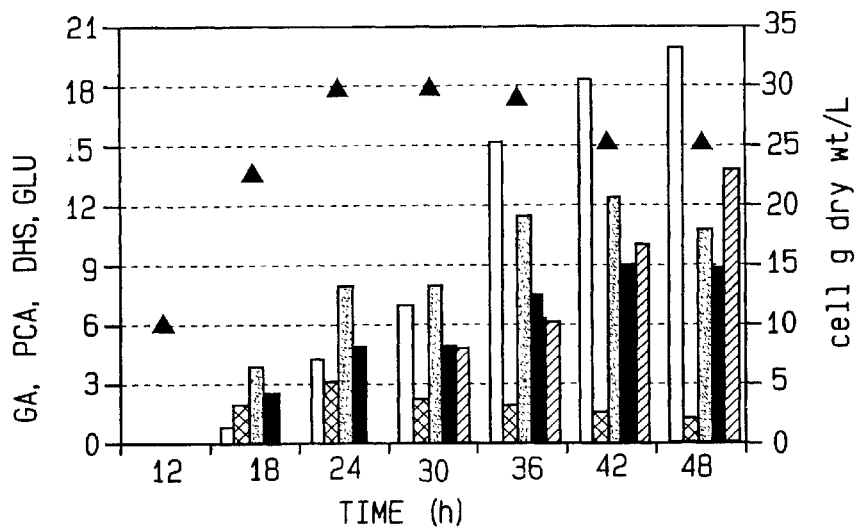
FIG. 3 is a graph showing the production of gallic acid by aerobic cultivation by *E. coli* KL7/pSK6.161.

Cultivation of *E. coli* KL7/pSK6.161 for 48 h in a fermentor under glucose-rich, nitrogen-rich culture conditions led to the formation of gallic acid (20 g/L), 3-deoxy-D-arabino-heptulosonic acid (DAH) (8.9 g/L), DHS (11 g/L), PCA (0.90 g/L), and glutamic acid (14 g/L) (FIG. 3). DAH accumulation was surprising given that this metabolite has not previously been observed when two genomic copies of aroB are expressed as in KL7 (Snell, K. D. et al., *J. Am. Chem. Soc.* 118:5605 (1996)). It was subsequently discovered that PCA competitively inhibits aroB-encoded 3-dehydroquinate synthase. The initial increase and subsequent decrease in PCA concentrations (FIG. 3) may indicate that KL7/pSK6.161 can recapture PCA initially exported into the culture medium. Glutamic acid accumulation can be traced to α-ketoglutarate and ultimately to pyruvate formed from phosphoenolpyruvate during the transport and phosphorylation of glucose. While not wishing to be bound by theory, it is believed that KL7/pSK6.161 is apparently converting this pyruvate via pyruvate dehydrogenase and Krebs cycle enzymes into $CO_2$ and α-ketoglutarate, which is transaminated and exported into the culture medium as glutamic acid. Gallic acid and PCA were extracted from cell-free culture supernatants using ethyl acetate (EtOAc). After concentration of the charcoal-decolorized organic layer, addition of petroleum ether led to precipitation of gallic acid as a white powder free of PCA contamination.

II. Materials and Methods

General. For $^1$H NMR quantitation of solute concentrations, solutions were concentrated to dryness under reduced pressure, concentrated to dryness one additional time from $D_2O$, and then redissolved in $D_2O$ containing a known concentration of the sodium salt of 3-(trimethylsilyl)propionic-2,2,3,3-$d_4$ acid (TSP) purchased from Lancaster Synthesis Inc. Concentrations were determined by comparison of integrals corresponding to each compound with the integral corresponding to TSP (δ=0.00 ppm) in the $^1$H NMR. All $^1$H NMR spectra were recorded on a Varian VXR-300 FT-NMR Spectrometer (300 MHz). Glucose concentrations in fermentation broths were measured using the Glucose Diagnostic Kit purchased from Sigma.

Culture Medium. All solutions were prepared in distilled, deionized water. LB medium contained (per L) Bacto tryptone (10 g), Bacto yeast extract (5 g), and NaCl (10 g). M9 salts contained (per L) $Na_2HPO_4$ (6 g), $KH_2PO_4$ (3 g), NaCl (0.5 g) and $NH_4Cl$ (1 g). M9 minimal medium (per L) consisted of 1 L of M9 salts containing D-glucose (10 g), $MgSO_4$ (0.12 g), and thiamine hydrochloride (0.001 g). Aromatic amino acid supplementation consisted of L-phenylalanine (40 mg/L), L-tyrosine (40 mg/L), L-tryptophan (40 mg/L), potassium p-aminobenzoate (10 mg/L), p-hydroxybenzoic acid (10 mg/L), and 2,3-dihydroxybenzoic acid (10 mg/L). Serine (40 mg/L) and shikimic acid (40 mg/L) supplementation were added where necessary. Ampicillin (50 mg/L) and chloramphenicol (20 mg/L) were added where appropriate. Solutions of inorganic salts, D-glucose, and MgSO4 were autoclaved separately. Thiamine, antibiotics, and growth supplements including amino acids and vitamins were sterilized through 0.22-μm membranes prior to addition to the medium. Solid medium was prepared by addition of 1.5% (w/v) Difco agar to the medium solution.

Fermentation medium (1 L) contained $K_2HPO_4$ (7.5 g), ammonium iron (III) citrate (0.3 g), citric acid monohydrate (2.1 g), L-phenylalanine (0.7 g), L-tyrosine (0.7 g), L-tryptophan (0.35 g), and concentrated $H_2SO_4$ (1.2 mL). Fermentation medium was adjusted to pH 7.0 by addition of concentrated $NH_4OH$ before autoclaving. The following supplements were added immediately prior to initiation of the fermentation: D-glucose (23 g or 30 g, as specified), $MgSO_4$ (0.24 g), p-hydroxybenzoic acid (0.010 g), potassium p-aminobenzoate (0.010 g), 2,3-dihydroxybenzoic acid (0.010 g), and trace minerals including $(NH_4)_6(Mo_7O_{24})$ $\cdot 4H_2O$ (0.0037 g), $ZnSO_4 \cdot 7H_2O$ (0.0029 g), $H_3BO_3$ (0.0247 g), $CuSO_4 \cdot 5H_2O$ (0.0025 g), and $MnCl_2 \cdot 4H_2O$ (0.0158 g). Inorganic salts containing the aromatic amino acid supplements were autoclaved separately from solutions of D-glucose and $MgSO_4$. Aromatic vitamins and trace minerals were sterilized through 0.22-$\mu$m membranes.

Genetic Manipulations. Standard procedures were used for construction, purification, and analysis of plasmid DNA. Sambrook, J., et al., *Molecular Cloning. A Laboratory Manual;* Cold Spring Harbor Laboratory: Plainview, N.Y. (1990). *E. coli* DH5α served as the host strain for all plasmid constructions. PCR amplifications were carried out as described by Sambrook (Sambrook, J. et al., *Molecular Cloning: A Laboratory Manual;* Cold Spring Harbor Laboratory: Plainview, N.Y. (1990)). Each reaction (0.1 mL) contained 10 mM KCl, 20 mM Tris-HCl (pH 8.8), 10 mM $(NH_4)_2SO_4$, 2 mM $MgSO_4$, 0.1% Triton X-100, dATP (0.2 mM), dCTP (0.2 mM), dGTP (0.2 mM), dTTP (0.2 mM), template DNA, 0.5 $\mu$M of each primer, and 2 units of Vent polymerase (New England Biolabs). Initial template concentrations varied from 0.02 to 1 $\mu$g.

Strain Construction. *E. coli* KL7 (Li, K. et al., *J. Am. Chem. Soc.* 120:10545 (1998)) was prepared by homologous recombination of an aroBaroZ cassette into the serA locus of AB2834 (Pittard, J. et al., *J. Bacteriol.* 91:1494 (1966)). Localization of the serA gene in pMAK705 (Hamilton, C. M. et al., *J. Bacteriol.* 171:4617 (1989)) followed by insertion of the aroBaroZ cassette into a restriction site internal to serA was used to direct recombination of the cassette into the serA locus of the genome. Plasmid pMAK705 contains a temperature-sensitive pSC101 replicon. Since derivatives of pMAK705 replicate at 30° C. but are unstable at 44° C., isolation of all pMAK705 derivatives required culturing at 30° C.

Digestion of pD2625 (GCI) with EcoR V and Dra I liberated a 1.9-kb serA fragment. Plasmid pMAK705 was digested with BamH I and modified to blunt ends by treatment with the Klenow fragment of DNA polymerase. Subsequent ligation of the serA fragment to pMAK705 afforded pLZ1.68A. The aroBaroZ cassette was created as follows. Plasmid pSK4.99A contains a 2.1 kb aroZ fragment inserted into the BamH I site of pSU18. The aroB gene was obtained as a 1.7 kb fragment following digestion of pJB14 (Frost, J. W. et al., *Biochemistry* 23:4470 (1984)) with EcoR I. After treatment with the Klenow fragment, the aroB-encoding fragment was cloned into the Sma I site of pSK4.99A to afford pKL4.237A. The resulting 3.9 kb aroBaroZ cassette of pKL4.237A was amplified by PCR such that BamH I recognition sequences were included at the 5'- and 3'-ends. Insertion of the cassette into the BamH I site of serA in pLZ1.68A yielded pKL4.276B. Both aroB and aroZ are transcribed in the opposite orientation relative to the lac promoter of pKL4.276B.

Conditions for homologous recombination were based on those previously described (Hamilton, C. M. et al., *J. Bacteriol.* 171:4617 (1989); Ohta, K. et al., *Appl. Environ. Microbiol.* 57:893 (1991)). Competent AB2834 cells were transformed with pKL4.276B. Following heat-shock treatment, cells were incubated in LB at 44° C. for 1 h and subsequently plated onto LB plates containing chloramphenicol. Plates were incubated at 44° C. for approximately 20 h before colonies appeared. The resulting colonies were inoculated into 5 mL of LB containing no antibiotics, and the cells were grown at 30° C. for 12 h to allow excision of the plasmid from the genome. Cultures were diluted (1:20000) in LB (5 mL) without antibiotics, and two more cycles of growth at 30° C. for 12 h were carried out to enrich cultures for more rapidly growing cells that had lost the temperature-sensitive replicon. Cultures were then diluted (1:20000) into LB and grown at 44° C. for 12 h to promote plasmid loss from the cells. Serial dilutions of each culture were spread onto LB plates and incubated at 30° C. overnight. The resulting colonies were screened on plates to select for recombined colonies. *E. coli* KL7 was isolated based on the following growth characteristics: growth on M9 containing L-tyrosine, L-phenylalanine, shikimic acid and serine; no growth on M9 containing L-tyrosine, L-phenylalanine, shikimic acid; growth on LB; and no growth on LB containing chloramphenicol.

pSK6.161. Plasmid pSK6.161 (FIG. 2) is an 8.8 kb pSU18-based plasmid that contains a 1.1 kb aroF$^{FBR}$-encoding insert, a 2.0 kb lacI$^q$-encoding insert, a 1.5 kb P$_{tac}$pobA*-encoding insert, and a 1.9 kb serA-encoding insert. Strains containing pSK6.161 are resistant to chloramphenicol. The 1.5 kb P$_{tac}$pobA* fragment originated from pSK4.176, a vector created by cloning a 1.2 kb PCR product encoding the pobA* ORF amplified from pIE130 (Entsch, B. et al., *J. Biol. Chem.* 266:17341 (1991)) into the EcoR I site of pKK223-3 (Brosius, J. et al., *PNAS (USA)* 81:6929 (1984)). Subsequent digestion of pSK4.176 with BamH I liberated a 1.5 kb P$_{tac}$pobA* fragment.

Fed-batch Fermentation. Cultures were grown in a 2.0 L capacity Biostat MD B-Braun fermentor connected to a DCU system and a Dell Optiplex Gs+5166M personal computer equipped with B-Braun MFCS/win software. The temperature and pH were controlled with a PID controller. Substrate feeding was controlled either manually or via PID controller. The temperature was maintained at 36° C. pH was maintained at 7.0 by addition of concentrated $NH_4OH$ or 2 N $H_2SO_4$. Dissolved oxygen (D.O.) was measured using a Braun polarographic probe and was set at either 10% or 20% air saturation, as indicated. Antifoam (Sigma 204) was pumped in manually as needed.

KL7/SK6.161 Fermentation. A single colony of KL7/pSK6.161 was inoculated into 5 mL of LB containing chloramphenicol and supplemented with glucose (4 g/L). Cells were grown overnight at 37° C. with agitation. Cells from 3 mL of the culture were harvested by centrifugation, washed in M9 salts, and used to inoculate 100 mL of M9 minimal medium (500 mL Erlenmeyer flask) containing D-glucose (8 g/L), aromatic amino acids and aromatic vitamin supplementation, and chloramphenicol. After growth at 37° C., 250 rpm for 12 h, the inoculant was ready for transfer into the fermentator vessel.

A set of stainless steel baffles was set inside the fermentation vessel to facilitate oxygen transfer. The initial glucose concentration in the fermentation medium was 30 g/L, and the fermentation was run at 36° C. After inoculation of the vessel, the fermentation process was divided into three stages according to three different methods used to maintain (D.O.) at the desired 10% air saturation during the course of the fermentation. With the airflow at an initial setting of 0.06 L/L/min, D.O. concentration was maintained by increasing the impeller speed from a preset minimum of 50 rpm to a preset maximum of 750 rpm. This first stage lasted approximately 10 h. With the impeller then held constant at 750 rpm, the mass flow controller maintained D.O. levels by increasing the airflow rate from 0.06 L/L/min to a preset maximum of 1.0 L/L/min. This second stage lasted approximately 2 h. In the final stage of control, which was utilized for the remainder of the fermentation, airflow was manually set at a point in the range of 1.0–1.65 L/L/min and the impeller speed was again allowed to vary to maintain the D.O. set point of 10% air saturation. Increasing the airflow above 1.0 L/L/min was necessary to maintain D.O. set point while keeping the impeller below a maximum desired value of 1500 rpm. During the third stage of the fermentation, addition of glucose (60% w/v) was controlled manually such that the glucose concentration was maintained in the range of 15–25 g/L. IPTG (30 mg) was added to the fermentation every 6 h starting 12 h after inoculation and continuing until the fermentation was complete.

Fermentation broth was harvested by centrifugation at 13000 g for 10 min, and the cells were discarded. Fermentation broth (450 ml) containing gallic acid (105 mM, 17.8 g/L), protocatechuic acid (5 mM, 0.78 g/L), 3-dehydroshikimic acid (15 mM, 2.5 g/L), 3-deoxy-D-arabino-heptulosonic acid (24 mM, 4.9 g/l), and glutamic acid (95 mM, 14 g/L) was adjusted to pH 2.3 by addition of concentrated $H_2SO_4$. After centrifugation at 13000 g for 10 min to remove precipitated protein, the aqueous solution was extracted three times with ethyl acetate (350 mL portions). The organic layers were combined and filtered under reduced pressure through a thin layer of Darco G-60 (100 mesh) activated charcoal in a buchner funnel. The filtrate was concentrated to 80 mL, mixed with 100 mL of petroleum ether, and chilled in an ice bath. Gallic acid (5.8 g, 72% isolated yield) was isolated as a white powder. NMR analysis of the powder confirmed it to comprise gallic acid ($^1$H NMR ($D_2O$) δ7.1 (s, 2H)).

SPECIFIC EXAMPLE 2

Biocatalytic Synthesis Of Gallic Acid From 3-Dehydroshikimic Acid

I. Results

Figure 4:
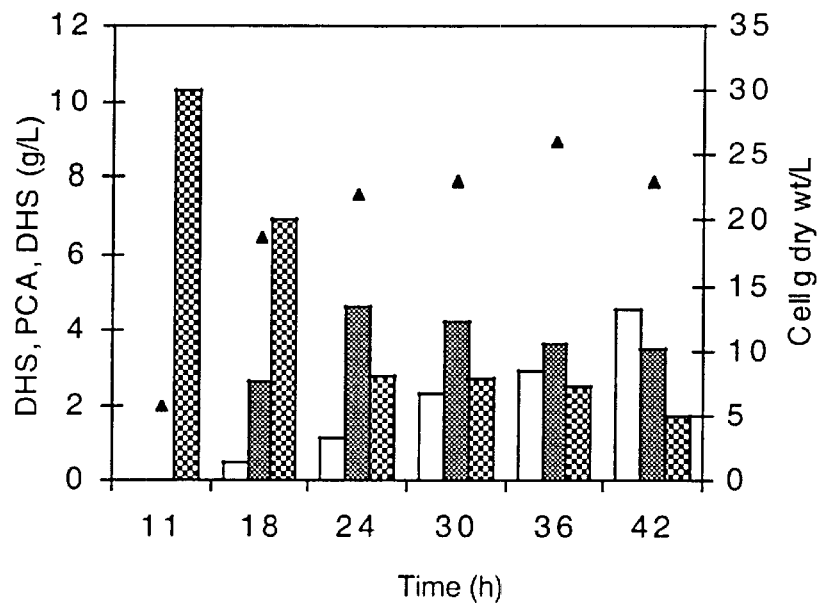
FIG. 4 is a graph showing the conversion of 3-dehydroshikmic acid to gallic acid by KL7/pSK6.76 when 3-dehydroshikimic acid was added to the cell culture in one portion.

Purified 3-dehydroshikimic acid was oxidized utilizing *E. coli* KL7/pSK6.76. Two different methods of 3-dehydroshikimic acid supplementation were used. In the first method, cells were grown until the maximum airflow was reached at 11 h, before a sterile-filtered solution (50 mL) of 3-dehydroshikimic acid (10.3 g,) was added in the culture supernatant (60 mM final concentration). Although the Lac repressor protein was not present in this plasmid, IPTG (15 mg) was added every 6 h starting at 12 h. Accumulation of protocatechuic acid was observed during the first 12 h following the 3-dehydroshikimic acid addition (24 h, FIG. 4) reaching a maximum value of 4.6 g/L and then slowly decreasing through the next 12 h (36 h, FIG. 4) reaching 3.5 g/L by the end of the fermentation run. At the same time 4/6 g/L of gallic acid were accumulated after 42 h of reaction time resulting in a 48% mol/mol yield based on added 3-dehydroshikimic acid (FIG. 4).

Figure 5:
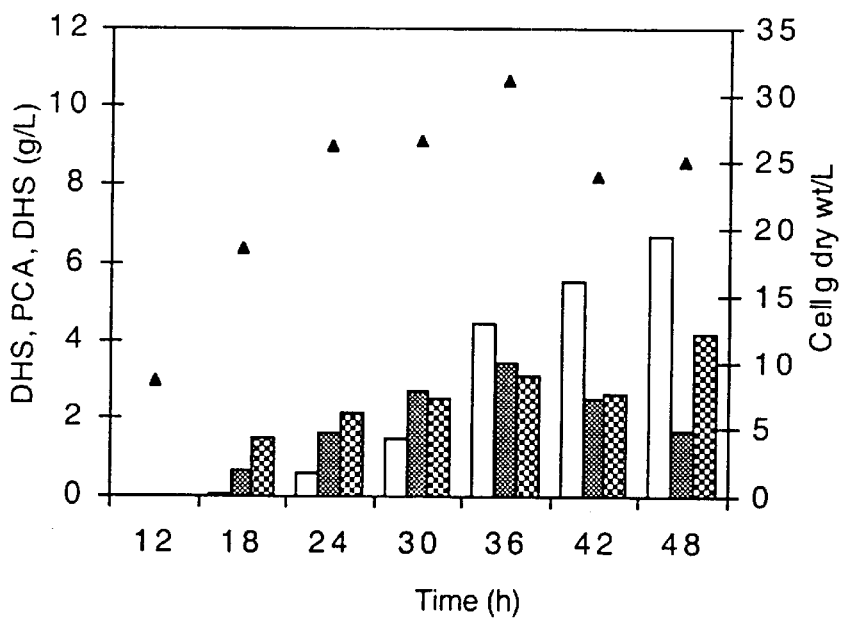
FIG. 5 is a graph showing the conversion of 3-dehydroshikimic acid to gallic acid by KL7/pSK6.76 when 3-dehydroshikimic acid was added in the cell culture with the glucose feed.

Alternatively, the 3-dehydroshikimic acid was added slowly with the glucose feed. The glucose feed solution was prepared by mixing 100 mL of a solution containing 18 g of 3-dehydroshikimic acid, with a 200 mL solution containing 120 g of glucose. An oxygen sensor controlled dissolved oxygen levels via addition of the solution containing glucose (0.4 g/mL) and 3-dehydroshikimic acid (0.06 g/mL, 0.35 mmol/mL). The rate of addition of the previous feed solution was about 8 mL/h and as a result approximately 0.5 g of 3-dehydroshikimic acid was added to the culture medium every hour. By the end of the fermentation run, the total amount of 3-dehydroshikimic acid added to the growing cells was 18 g, producing 6.3 g/L of gallic acid at 48 h in a 45% (mol/mol) yield based on added 3-dehydroshikimic acid. Significant amounts of protocatechuic acid (1.8 g/L) as well as unreacted 3-dehydroshikimic acid (4.2 g/L) were present at the end of the run (FIG. 5). A 20 mL aliquot of fermentation broth was taken at 24 h, 36 h, and 48 h for determination of PHB hydroxylase activity. Although pobA* activities were stable throughout the fermentation, the majority of gallic acid was produced in stationary phase (after 24 h). Interestingly, the concentration of protocatechuic acid showed an initial increase reaching a maximum value of 3.4 g/L at 36 h, after which the concentration of protocatechuic acid steadily decreased to 1.8 g/L at 48 h (FIG. 5).

II. Materials and Methods

General. For $^1$H NMR quantitation of solute concentrations, solutions were concentrated to dryness under reduced pressure, concentrated to dryness one additional time from $D_2O$, and then redissolved in $D_2O$ containing a known concentration of the sodium salt of 3-(trimethylsilyl)propionic-2,2,3,3-$d_4$ acid (TSP) purchased from Lancaster Synthesis Inc. Concentrations were determined by comparison of integrals corresponding to each compound with the integral corresponding to TSP (δ=0.00 ppm) in the $^1$H NMR. All $^1$H NMR spectra were recorded on a Varian VXR-300 FT-NMR Spectrometer (300 MHz). Glucose concentrations in fermentation broths were measured using the Glucose Diagnostic Kit purchased from Sigma.

Culture Medium. All solutions were prepared in distilled, deionized water. LB medium contained (per L) Bacto tryptone (10 g), Bacto yeast extract (5 g), and NaCl (10 g). M9 salts contained (per L) $Na_2HPO_4$ (6 g), $KH_2PO_4$ (3 g), NaCl (0.5 g) and $NH_4Cl$ (1 g). M9 minimal medium (per L) consisted of 1 L of M9 salts containing D-glucose (10 g), $MgSO_4$ (0.12 g), and thiamine hydrochloride (0.001 g). Aromatic amino acid supplementation consisted of L-phenylalanine (40 mg/L), L-tyrosine (40 mg/L), L-tryptophan (40 mg/L), potassium p-aminobenzoate (10 mg/L), p-hydroxybenzoic acid (10 mg/L), and 2,3-dihydroxybenzoic acid (10 mg/L). Serine (40 mg/L) and shikimic acid (40 mg/L) supplementation were added where necessary. Ampicillin (50 mg/L) and chloramphenicol (20 mg/L) were added where appropriate. Solutions of inorganic salts, D-glucose, and $MgSO_4$ were autoclaved separately. Thiamine, antibiotics, and growth supplements including amino acids and vitamins were sterilized through 0.22-μm membranes prior to addition to the medium. Solid medium was prepared by addition of 1.5% (w/v) Difco agar to the medium solution.

Fermentation medium (1 L) contained $K_2HPO_4$ (7.5 g), ammonium iron (III) citrate (0.3 g), citric acid monohydrate (2.1 g), L-phenylalanine (0.7 g), L-tyrosine (0.7 g), L-tryptophan (0.35 g), and concentrated $H_2SO_4$ (1.2 mL). Fermentation medium was adjusted to pH 7.0 by addition of concentrated $NH_4OH$ before autoclaving. The following supplements were added immediately prior to initiation of the fermentation: D-glucose (23 g or 30 g, as specified), $MgSO_4$ (0.24 g), p-hydroxybenzoic acid (0.010 g), potassium p-aminobenzoate (0.010 g), 2,3-dihydroxybenzoic acid (0.010 g), and trace minerals including $(NH_4)_6(Mo_7O_{24}).4H_2O$ (0.0037 g), $ZnSO_4.7H_2O$ (0.0029 g), $H_3BO_3$ (0.0247 g), $CuSO_4.5H_2O$ (0.0025 g), and $MnCl_2.4H_2O$ (0.0158 g). Inorganic salts containing the aromatic amino acid supplements were autoclaved separately from solutions of D-glucose and MgSO4 Aromatic vitamins and trace minerals were sterilized through 0.22-μm membranes.

Genetic Manipulations. Standard procedures were used for construction, purification, and analysis of plasmid DNA (Sambrook, J., et al., *Molecular Cloning: A Laboratory Manual;* Cold Spring Harbor Laboratory: Plainview, N.Y. (1990)). *E. coli* DH5α served as the host strain for all plasmid constructions. PCR amplifications were carried out as described by Sambrook (Sambrook, J. et al., *Molecular Cloning: A Laboratory Manual;* Cold Spring Harbor Laboratory: Plainview, N.Y. (1990)). Each reaction (0.1 mL) contained 10 mM KCl, 20 mM Tris-HCl (pH 8.8), 10 mM $(NH_4)_2SO_4$, 2 mM $MgSO_4$, 0.1% Triton X-100, dATP (0.2 mM), dCTP (0.2 mM), dGTP (0.2 mM), dTTP (0.2 mM), template DNA, 0.5 μM of each primer, and 2 units of Vent polymerase (New England Biolabs). Initial template concentrations varied from 0.02 to 1 μg.

Strain Construction. *E. coli* KL7 (Li, K. et al., *J. Am. Chem. Soc.* 120:10545 (1998)) was prepared by homologous recombination of an aroBaroZ cassette into the sera locus of AB2834 (Pittard, J. et al., *J. Bacteriol.* 91:1494 (1966)). Localization of the serA gene in pMAK705 (Hamilton, C. M. et al., *J. Bacteriol.* 171:4617 (1989)) followed by insertion of the aroBaroZ cassette into a restriction site internal to serA was used to direct recombination of the cassette into the serA locus of the genome. Plasmid pMAK705 contains a temperature-sensitive pSC101 replicon. Since derivatives of pMAK705 replicate at 30° C. but are unstable at 44° C., isolation of all pMAK705 derivatives required culturing at 30° C.

Digestion of pD2625 (GCI) with EcoR V and Dra I liberated a 1.9-kb serA fragment. Plasmid pMAK705 was digested with BamH I and modified to blunt ends by treatment with the Klenow fragment of DNA polymerase. Subsequent ligation of the serA fragment to pMAK705 afforded pLZ1.68A. The aroBaroZ cassette was created as follows. Plasmid pSK4.99A contains a 2.1 kb aroZ fragment inserted into the BamH I site of pSU18. The aroB gene was obtained as a 1.7 kb fragment following digestion of pJB14 (Frost, J. W. et al., *Biochemistry* 23:4470 (1984)) with EcoR I. After treatment with the Klenow fragment, the aroB-encoding fragment was cloned into the Sma I site of pSK4.99A to afford pKL4.237A. The resulting 3.9 kb aroBaroZ cassette of pKL4.237A was amplified by PCR such that BamH I recognition sequences were included at the 5'- and 3'-ends. Insertion of the cassette into the BamH I site of serA in pLZ1.68A yielded pKL4.276B. Both aroB and aroZ are transcribed in the opposite orientation relative to the lac promoter of pKL4.276B.

Conditions for homologous recombination were based on those previously described (Hamilton, C. M. et al., *J. Bacteriol.* 171:4617 (1989); Ohta, K. et al., *Appl. Environ. Microbiol.* 57:893 (1991)). Competent AB2834 cells were transformed with pKL4.276B. Following heat-shock treatment, cells were incubated in LB at 44° C. for 1 h and subsequently plated onto LB plates containing chloramphenicol. Plates were incubated at 44° C. for approximately 20 h before colonies appeared. The resulting colonies were inoculated into 5 mL of LB containing no antibiotics, and the cells were grown at 30° C. for 12 h to allow excision of the plasmid from the genome. Cultures were diluted (1:20000) in LB (5 mL) without antibiotics, and two more cycles of growth at 30° C. for 12 h were carried out to enrich cultures for more rapidly growing cells that had lost the temperature-sensitive replicon. Cultures were then diluted (1:20000) into LB and grown at 44° C. for 12 h to promote plasmid loss from the cells. Serial dilutions of each culture were spread onto LB plates and incubated at 30° C. overnight. The resulting colonies were screened on plates to select for recombined colonies. *E. coli* KL7 was isolated based on the following growth characteristics: growth on M9 containing L-tyrosine, L-phenylalanine, shikimic acid and serine; no growth on M9 containing L-tyrosine, L-phenylalanine, shikimic acid; growth on LB; and no growth on LB containing chloramphenicol.

pSK6.76. Plasmid pSK6.76 is a 7.8 kb pSU18-based plasmid that contains a 1.1 kb $aroF^{FBR}$-encoding insert, a 1.5 kb $P_{tac}$pobA*-encoding insert, and a 1.9 kb serA-encoding insert. Strains containing pSK6.76 are resistant to chloramphenicol. The 1.5 kb $P_{tac}$pobA* fragment originated from pSK4.176, a vector created by cloning a 1.2 kb PCR product encoding the pobA* ORF amplified from pE130 (Entsch, B. et al., *J. Biol. Chem.* 266:17341 (1991)) into the EcoR I site of pKK223-3 (Brosius, J. et al., *PNAS (USA)* 81:6929 (1984)). Subsequent digestion of pSK4.176 with BamH I liberated a 1.5 kb $P_{tac}$pobA* fragment.

Fed-batch Fermentation. Cultures were grown in a 2.0 L capacity Biostat MD B-Braun fermentor connected to a DCU system and a Dell Optiplex Gs+5166M personal computer equipped with B-Braun MFCS/win software. The temperature and pH were controlled with a PID controller. Substrate feeding was controlled either manually or via PID controller. The temperature was maintained at 36° C. pH was maintained at 7.0 by addition of concentrated $NH_4OH$ or 2 N $H_2SO_4$. Dissolved oxygen (D.O.) was measured using a Braun polarographic probe and was set at either 10% or 20% air saturation, as indicated. Antifoam (Sigma 204) was pumped in manually as needed.

KL7/SK6.76 Fermentation. A single colony of KL7/pSK6.76 was inoculated into 5 mL of LB containing chloramphenicol and supplemented with glucose (4 g/L). Cells were grown overnight at 37° C. with agitation. Cells from 3 mL of the culture were harvested by centrifugation, washed in M9 salts, and used to inoculate 100 mL of M9 minimal medium (500 mL Erlenmeyer flask) containing D-glucose (8 g/L), aromatic amino acids and aromatic vitamin supplementation, and chloramphenicol. After growth at 37° C. , 250 rpm for 12 h, the inoculant was ready for transfer into the fermentator vessel.

A set of stainless steel baffles was set inside the fermentation vessel to facilitate oxygen transfer. The initial glucose concentration in the fermentation medium was 23 g/L, and the fermentation was run at 360° C. After inoculation of the vessel, the fermentation process was divided into three stages according to three different methods used to maintain (D.O.) at the desired 10% air saturation during the course of the fermentation. With the airflow at an initial setting of 0.06 L/L/min, D.O. concentration was maintained by increasing the impeller speed from a preset minimum of 50 rpm to a preset maximum of 750 rpm. This first stage lasted approximately 10 h. A sterile filtered aqueous solution of DHS (10.3 g, 6 mmol in 50 ml $H_2O$, pH 6.9) was then added as a single addition. With the impeller then held constant at 750 rpm, the mass flow controller maintained D.O. levels by increasing the airflow rate from 0.06 L/L/min to a preset maximum of 1.0 L/L/min. This second stage lasted approximately 2 h. In the final stage of control, which was utilized for the remainder of the fermentation, airflow was manually set at a point in the range of 1.0-1.65 L/L/min and the impeller speed was again allowed to vary to maintain the D.O. set point of 10% air saturation. Increasing the airflow above 1.0 L/L/min was necessary to maintain D.O. set point while keeping the impeller below a maximum desired value of 1500 rpm. During the third stage of the fermentation, addition of glucose (60% w/v) was controlled manually such that the glucose concentration was maintained in the range of 15–25 g/L. For addition of DHS with the glucose feed, a filter-sterilized solution of DHS (18 g in 100 ml $H_2O$, pH 6.8) was added to the glucose solution. IPTG (30 mg) was added to the fermentation every 6 h starting 12 h after inoculation and continuing until the fermentation was complete.

Samples (5 mL) of fermentation broth were taken at timed intervals. A portion (1 mL) was used to determine the cell density by measuring the absorption at 600 nm ($OD_{600}$). The remaining 4 mL of each fermentation broth sample was centrifuged using a Beckman microfuge. A portion (0.5–2 mL) of the culture supernatant was used for $^1H$ NMR analysis. The $OD_{600}$ was converted to the cell dry weight by using a conversion coefficient determined as follows: Fermentation broth with a known $OD_{600}$ was centrifuged, and all the cells were collected. After washing three times with fresh M9 salts (400 mL), the cells were transferred to a container and dried in a 100° C. oven until the weight was constant. The dry cell weight was determined and a conversion coefficient (dry cell weight/$OD_{600}$) of 0.43 was obtained using an average value of three experiments.

SPECIFIC EXAMPLE 3

Biocatalytic Synthesis of Gallic Acid from Protocatechuic Acid

I. Results

The conversion of 3-dehydroshikimic acid into gallic acid using intact *E. coli* cells demonstrated the ability of this microbe to transport 3-dehydroshikimic acid. More importantly, the intracellular formation of $H_2O_2$ and gallic acid, both resulting from pobA* expression, were not sufficient to preclude microbe viability and gallic acid synthesis. Furthermore, the decline in the concentration of protocatechuic acid in the culture supernatant of KL7/pSK6.76 during the final 12 h of continuous 3-dehydroshikimate addition suggested that protocatechuic acid transport into the cytoplasm was occurring. Previous literature precedent indicated that *E. coli* was incapable of transporting protocatechuic acid into its cytoplasm form the culture supernatants. Nichols, N. N. et al., *J. Bacteriol.* 177:7033 (1995); Nichols, N. N. et al., *J. Bacteriol.* 179:5056 (1997). In agreement with the literature, cultivation of KL7/pSK6.118 under shaken flask conditions in the presence of protocatechuic acid showed essentially no gallic acid formation, with the concentration of protocatechuic acid remaining unchanged after 24 h of cultivation.

Figure 6:
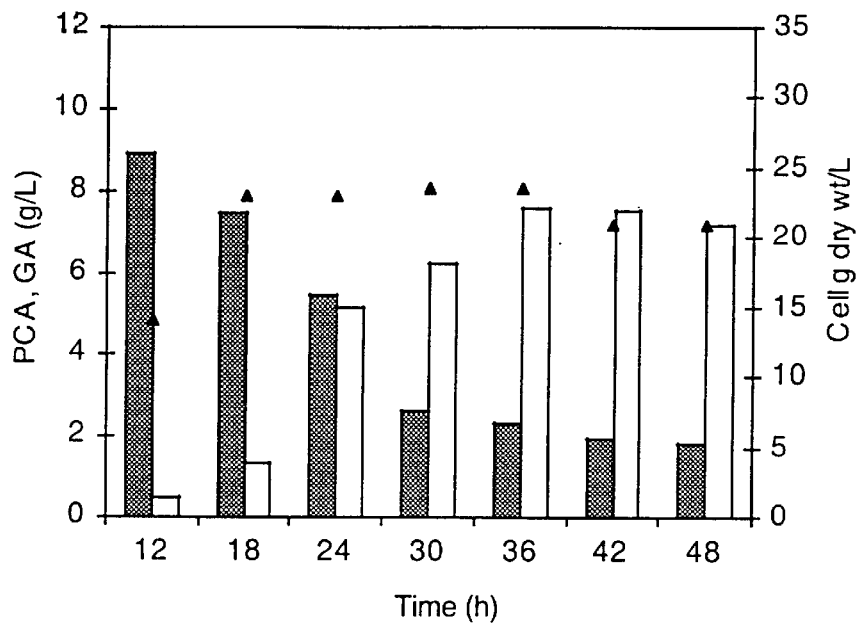
FIG. 6 is a graph showing the conversion of protocatechuic acid to gallic acid by KL7/pSK6.118 when protocatechuic acid was added to the cell culture in one portion.

However, when KL7/pSK6.118 was cultured under fed-batch fermentor conditions, 7.7 g/L of gallic acid was synthesized (FIG. 6) after addition of protocatechuic acid (9 g) in one portion when the maximum airflow rate of 10 h was reached. The yield (mol/mol) of the gallic acid formation based on the 3-dehydroshikmic acid added in the fermentation broth was 80%. The decrease in protocatechuic concentration corresponded to an approximately equimolar increase in gallic acid concentration. Apparently, recombinant *E. coli* cultured under fed-batch fermentor conditions is capable of protocatechuate transport into its cytoplasm.

Figure 7:
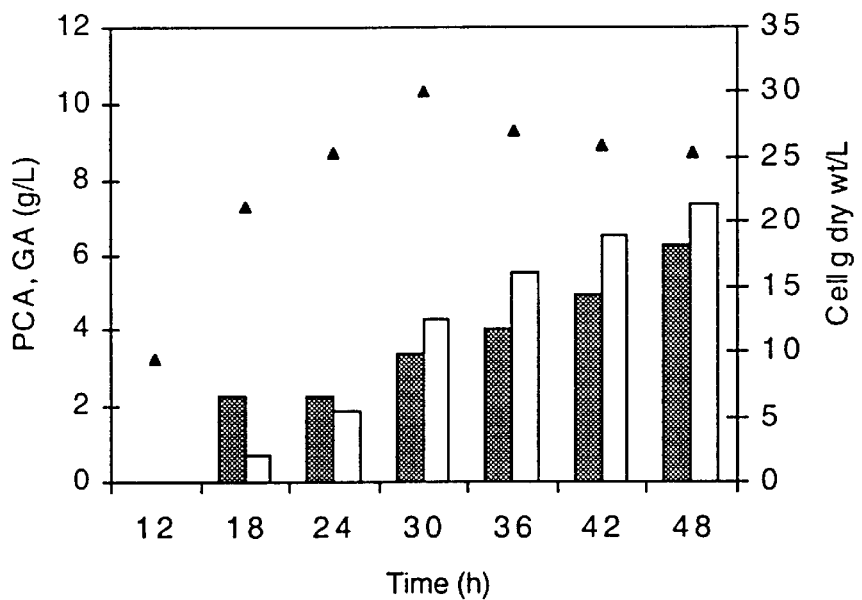
FIG. 7 is a graph showing the conversion of protocatechuic acid to gallic acid by KL7/pSK6.118 when protocatechuic acid was added to the cell culture with the glucose feed.

The same gallic acid titer (7.3 g/L) was produced if instead of one portion, protocatechuic acid was added slowly with the glucose feed (FIG. 7). An oxygen sensor was used to control dissolved oxygen levels in the culture medium via glucose addition. The feeding solution contained glucose (0.4 g/mL) and 0.053 g/mL (0.34 mol/mL) of protocatechuic acid, and as a result, the addition of this metabolite was controlled from the rate of glucose consumption by the biocatalyst. The feeding rate was about 7.5 mL/h resulting in addition of around 0.4 g of protocatechuic acid per hour. The yield (mol/mol) of gallic acid synthesized based on protocatechuic acid addition to the fermentation broth was 54%. Addition of IPTG (15 mg) every 6 h starting from the time of maximum airflow was necessary to induce the mutant p-hydroxybenzoate hydroxylase expression (0.038 U/mg). In contrast to pSK6.76 plasmid, plasmid pSK6.118 carries the repressor Lac protein and IPTG addition was necessary for adequate expression of the hydroxylase. Comparable activities of the hydroxylase were obtained during synthesis of gallic acid from 3-dehydroshikimic acid and during synthesis of gallic acid from protocatechuic acid. However, addition of protocatechuic acid resulted in an increase of 1 g/L of gallic acid compared to 3-dehydroshikimic acid supplementation.

II. Materials and Methods

General. For $^1H$ NMR quantitation of solute concentrations, solutions were concentrated to dryness under reduced pressure, concentrated to dryness one additional time from $D_2O$, and then redissolved in $D_2O$ containing a known concentration of the sodium salt of 3-(trimethylsilyl)propionic-2,2,3,3-$d_4$ acid (TSP) purchased from Lancaster Synthesis Inc. Concentrations were determined by comparison of integrals corresponding to each compound with the integral corresponding to TSP ($\delta$=0.00 ppm) in the $^1H$ NMR. All $^1H$ NMR spectra were recorded on a Varian VXR-300 FT-NMR Spectrometer (300 MHz). Glucose concentrations in fermentation broths were measured using the Glucose Diagnostic Kit purchased from Sigma.

Culture Medium. All solutions were prepared in distilled, deionized water. LB medium contained (per L) Bacto tryptone (10 g), Bacto yeast extract (5 g), and NaCl (10 g). M9 salts contained (per L) $Na_2HPO_4$ (6 g), $KH_2PO_4$ (3 g), NaCl (0.5 g) and $NH_4Cl$ (1 g). M9 minimal medium (per L) consisted of 1 L of M9 salts containing D-glucose (10 g), $MgSO_4$ (0.12 g), and thiamine hydrochloride (0.001 g). Aromatic amino acid supplementation consisted of L-phenylalanine (40 mg/L), L-tyrosine (40 mg/L), L-tryptophan (40 mg/L), potassium p-aminobenzoate (10 mg/L), p-hydroxybenzoic acid (10 mg/L), and 2,3-dihydroxybenzoic acid (10 mg/L). Serine (40 mg/L) and shikimic acid (40 mg/L) supplementation were added where necessary. Ampicillin (50 mg/L) and chloramphenicol (20 mg/L) were added where appropriate. Solutions of inorganic salts, D-glucose, and $MgSO_4$ were autoclaved separately. Thiamine, antibiotics, and growth supplements including amino acids and vitamins were sterilized through 0.22-$\mu$m membranes prior to addition to the medium. Solid medium was prepared by addition of 1.5% (w/v) Difco agar to the medium solution.

Fermentation medium (1 L) contained $K_2HPO_4$ (7.5 g), ammonium iron (III) citrate (0.3 g), citric acid monohydrate (2.1 g), L-phenylalanine (0.7 g), L-tyrosine (0.7 g), L-tryptophan (0.35 g), and concentrated $H_2SO_4$ (1.2 mL). Fermentation medium was adjusted to pH 7.0 by addition of concentrated $NH_4OH$ before autoclaving. The following supplements were added immediately prior to initiation of the fermentation: D-glucose (23 g or 30 g, as specified), $MgSO_4$ (0.24 g), p-hydroxybenzoic acid (0.010 g), potassium p-aminobenzoate (0.010 g), 2,3-dihydroxybenzoic acid (0.010 g), and trace minerals including $(NH_4)_6(Mo_7O_{24})$·$4H_2O$ (0.0037 g), $ZnSO_4$·$7H_2O$ (0.0029 g), $H_3BO_3$ (0.0247 g), $CuSO_4$·$5H_2O$ (0.0025 g), and $MnCl_2$·$4H_2O$ (0.0158 g). Inorganic salts containing the aromatic amino acid supplements were autoclaved separately from solutions of D-glucose and MgSO$_4$. Aromatic vitamins and trace minerals were sterilized through 0.22-μm membranes.

Genetic Manipulations. Standard procedures were used for construction, purification, and analysis of plasmid DNA (Sambrook, J., et al., *Molecular Cloning: A Laboratory Manual;* Cold Spring Harbor Laboratory: Plainview, N.Y. (1990)). *E. coli* DH5α served as the host strain for all plasmid constructions. PCR amplifications were carried out as described by Sambrook (Sambrook, J. et al., *Molecular Cloning: A Laboratory Manual;* Cold Spring Harbor Laboratory: Plainview, N.Y. (1990)). Each reaction (0.1 mL) contained 10 mM KCl, 20 mM Tris-HCl (pH 8.8), 10 mM (NH$_4$)$_2$SO$_4$, 2 mM MgSO$_4$, 0.1% Triton X-100, dATP (0.2 mM), dCTP (0.2 mM), dGTP (0.2 mM), dTTP (0.2 mM), template DNA, 0.5 μM of each primer, and 2 units of Vent polymerase (New England Biolabs). Initial template concentrations varied from 0.02 to 1 μg.

Strain Construction. *E. coli* KL7 (Li, K. et al., *J. Am. Chem. Soc.* 120:10545 (1998)) was prepared by homologous recombination of an aroBaroZ cassette into the serA locus of AB2834 (Pittard, J. et al., *J. Bacteriol.* 91:1494 (1966)). Localization of the serA gene in pMAK705 (Hamilton, C. M. et al., *J. Bacteriol.* 171:4617 (1989)) followed by insertion of the aroBaroZ cassette into a restriction site internal to serA was used to direct recombination of the cassette into the serA locus of the genome. Plasmid pMAK705 contains a temperature-sensitive pSC101 replicon. Since derivatives of pMAK705 replicate at 30° C. but are unstable at 44° C., isolation of all pMAK705 derivatives required culturing at 30° C.

Digestion of pD2625 (GCI) with EcoR V and Dra I liberated a 1.9-kb serA fragment. Plasmid pMAK705 was digested with BamH I and modified to blunt ends by treatment with the Klenow fragment of DNA polymerase. Subsequent ligation of the serA fragment to pMAK705 afforded pLZ1.68A. The aroBaroZ cassette was created as follows. Plasmid pSK4.99A contains a 2.1 kb aroZ fragment inserted into the BamH I site of pSU18. The aroB gene was obtained as a 1.7 kb fragment following digestion of pJB14 (Frost, J. W. et al., *Biochemistry* 23:4470 (1984)) with EcoR I. After treatment with the Klenow fragment, the aroB-encoding fragment was cloned into the Sma I site of pSK4.99A to afford pKL4.237A. The resulting 3.9 kb aroBaroZ cassette of pKL4.237A was amplified by PCR such that BamH I recognition sequences were included at the 5'- and 3'-ends. Insertion of the cassette into the BamH I site of serA in pLZ1.68A yielded pKL4.276B. Both aroB and aroZ are transcribed in the opposite orientation relative to the lac promoter of pKL4.276B.

Conditions for homologous recombination were based on those previously described (Hamilton, C. M. et al., *J. Bacteriol.* 171:4617 (1989); Ohta, K. et al., *Appl. Environ. Microbiol* 57:893 (1991)). Competent AB2834 cells were transformed with pKL4.276B. Following heat-shock treatment, cells were incubated in LB at 44° C. for 1 h and subsequently plated onto LB plates containing chloramphenicol. Plates were incubated at 44° C. for approximately 20 h before colonies appeared. The resulting colonies were inoculated into 5 mL of LB containing no antibiotics, and the cells were grown at 30° C. for 12 h to allow excision of the plasmid from the genome. Cultures were diluted (1:20000) in LB (5 mL) without antibiotics, and two more cycles of growth at 30° C. for 12 h were carried out to enrich cultures for more rapidly growing cells that had lost the temperature-sensitive replicon. Cultures were then diluted (1:20000) into LB and grown at 44° C. for 12 h to promote plasmid loss from the cells. Serial dilutions of each culture were spread onto LB plates and incubated at 30° C. overnight. The resulting colonies were screened on plates to select for recombined colonies. *E. coli* KL7 was isolated based on the following growth characteristics: growth on M9 containing L-tyrosine, L-phenylalanine, shikimic acid and serine; no growth on M9 containing L-tyrosine, L-phenylalanine, shikimic acid; growth on LB; and no growth on LB containing chloramphenicol.

pSK6.118. Plasmid pSK6.118 is a 7.6 kb pSU18-based plasmid that contains a 2.0 kb lacI$^q$-encoding insert, a 1.5 kb P$_{tac}$pobA*-encoding insert, and a 1.9 kb serA-encoding insert. Strains containing pSK6.118 are resistant to chloramphenicol. The 1.5 kb P$_{tac}$pobA* fragment originated from pSK4.176, a vector created by cloning a 1.2 kb PCR product encoding the pobA* ORF amplified from pIE130 (Entsch, B. et al., *J. Biol. Chem.* 266:17341 (1991)) into the EcoR I site of pKK223-3 (Brosius, J. et al., *PNAS (USA)* 81:6929 (1984)). Subsequent digestion of pSK4.176 with BamH I liberated a 1.5 kb P$_{tac}$pobA* fragment.

Fed-batch Fermentation. Cultures were grown in a 2.0 L capacity Biostat MD B-Braun fermentor connected to a DCU system and a Dell Optiplex Gs+ 5166M personal computer equipped with B-Braun MFCS/win software. The temperature and pH were controlled with a PID controller. Substrate feeding was controlled either manually or via PID controller. The temperature was maintained at 36° C. pH was maintained at 7.0 by addition of concentrated NH$_4$OH or 2 N H$_2$SO$_4$. Dissolved oxygen (D.O.) was measured using a Braun polarographic probe and was set at either 10% or 20% air saturation, as indicated. Antifoam (Sigma 204) was pumped in manually as needed.

KL7/SK6.118 Fermentation. A single colony of KL7/pSK6.118 was inoculated into 5 mL of LB containing chloramphenicol and supplemented with glucose (4 g/L). Cells were grown overnight at 37° C. with agitation. Cells from 3 mL of the culture were harvested by centrifugation, washed in M9 salts, and used to inoculate 100 mL of M9 minimal medium (500 mL Erlenmeyer flask) containing D-glucose (8 g/L), aromatic amino acids and aromatic vitamin supplementation, and chloramphenicol. After growth at 37° C., 250 rpm for 12 h, the inoculant was ready for transfer into the fermentator vessel.

A set of stainless steel baffles was set inside the fermentation vessel to facilitate oxygen transfer. The initial glucose concentration in the fermentation medium was 23 g/L, and the fermentation was run at 36° C. After inoculation of the vessel, the fermentation process was divided into three stages according to three different methods used to maintain (D.O.) at the desired 10% air saturation during the course of the fermentation. With the airflow at an initial setting of 0.06 L/L/min, D.O. concentration was maintained by increasing the impeller speed from a preset minimum of 50 rpm to a preset maximum of 750 rpm. This first stage lasted approximately 10 h. For a one time addition, a sterile solution of PCA was added (9 g in 50 ml H$_2$O, pH 6.8). With the impeller then held constant at 750 rpm, the mass flow controller maintained D.O. levels by increasing the airflow rate from 0.06 L/L/min to a preset maximum of 1.0 L/L/min. This second stage lasted approximately 2 h. In the final stage of control, which was utilized for the remainder of the fermentation, airflow was manually set at a point in the range of 1.0–1.65 L/L/min and the impeller speed was again allowed to vary to maintain the D.O. set point of 10% air saturation. Increasing the airflow above 1.0 L/L/min was necessary to maintain D.O. Let point while keeping the impeller below a maximum desired value of 1500 rpm. During the third stage of the fermentation, addition of glucose (60% w/v) was controlled manually such that the glucose concentration was maintained in the range of 15–25 g/L. For addition with the glucose feed, a sterile solution of PCA (16 g in 100 ml $H_2O$, pH 6.8) was added to the glucose. IPTG (30 mg) was added to the fermentation every 6 h starting 12 h after inoculation and continuing until the fermentation was complete.

Samples (5 mL) of fermentation broth were taken at timed intervals. A portion (1 mL) was used to determine the cell density by measuring the absorption at 600 nm ($OD_{600}$). The remaining 4 mL of each fermentation broth sample was centrifuged using a Beckman microfuge. A portion (0.5–2 mL) of the culture supernatant was used for $^1H$ NMR analysis. The $OD_{600}$ was converted to the cell dry weight by using a conversion coefficient determined as follows: Fermentation broth with a known $OD_{600}$ was centrifuged, and all the cells were collected. After washing three times with fresh M9 salts (400 mL), the cells were transferred to a container and dried in a 100° C. oven until the weight was constant. The dry cell weight was determined and a conversion coefficient (dry cell weight/OD600) of 0.43 was obtained using an average value of three experiments.

SPECIFIC EXAMPLE 4

Biocatalytic Synthesis Of Pyrogallol From Gallic Acid

I. Results

Pyrogallol is typically generated as a catabolic intermediate by microbes using either gallic acid or tannic acid as a sole source of carbon during growth (Armstrong, S. M. et al., *J. Basic Microbiol.* 34:123 (1994)). The most extensively characterized nonoxidative decarboxylase capable of converting gallic acid into pyrogallol has been isolated from *Pantoea agglomerans* T71 (Zeida, M. et al., *Appl. Environ. Micriobiol.* 64:4743 (1998)). In the present invention, the conversion of gallic acid into pyrogallol was based on the fortuitous discovery that aroY-encoded PTA decarboxylase (Draths, K. M. et al., *J. Am. Chem. Soc.* 116:399 (1994); Draths, K. M. et al., *In Benign by Design;* Anasta, P. T.; Farris C. S. Ed.; ACS Symposium Series 577; American Chemical Society: Wash., D.C., Chap. 3, p. 32 (1994); Draths, K. M. et al., *J. Am. Chem. Soc.* 117:2395 (1995)) isolated from *K. pneumoniae* also catalyzes the decarboxylation of gallic acid to pyrogallol. PCA decarboxylase has previously been used in microbial syntheses of catechol and adipic acid from glucose (Draths, K. M. et al., *J. Am. Chem. Soc.* 116:399 (1994); Draths, K. M. et al., *In Benign by Design;* Anasta, P. T.; Farris C. S. Ed.; ACS Symposium Series 577; American Chemical Society: Wash., D.C., Chap. 3, p. 32 (1994); Draths, K. M. et al., *J. Am. Chem. Soc.* 117:2395 (1995)).

Synthesis of pyrogallol from glucose was attempted using *E. coli* KL7/pSK6.232. Plasmid pSK6.232 carried an aroY insert in addition to serA, $P_{tac}$ pobA*, $lacI^q$, and $P_{tac}aroF^{FBR}$. KL7/pSK6.232 cultured under fermentor conditions failed to grow beyond 18 h of cultivation and dissolved $O_2$ levels could not be controlled after 24 h. Neither gallic acid or pyrogallol formation could be detected. Only formation of catechol was observed suggesting that the rate of in vivo decarboxylation of PCA was significantly more rapid than mutant p-hydroxybenzoate hydroxylase-catalyzed hydroxylation of PCA. Catechol formation and its associated toxicity (Draths, K. M. et al., *J. Am. Chem. Soc.* 117:2395 (1995)) towards microbes may explain the early cessation of growth and loss of dissolved $O_2$ control.

Figure 8:
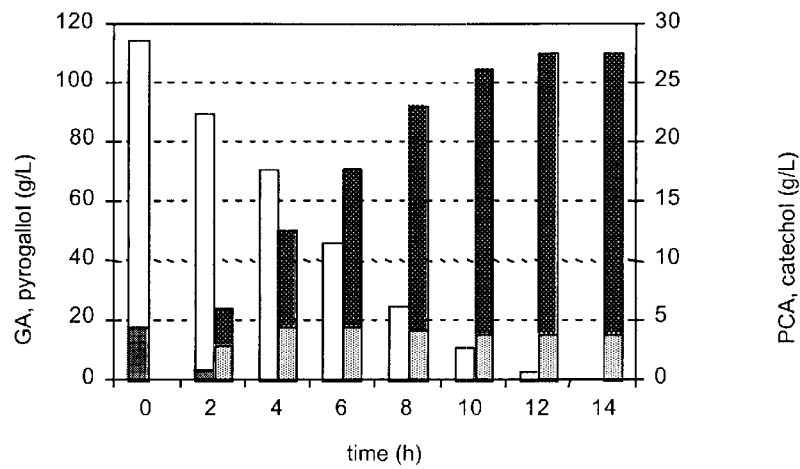
FIG. 8 is a graph showing the conversion of gallic acid to pyrogallol catalyzed by RB791 serA::aroB/pSK6.234.

Synthesis of pyrogallol subsequently switched to a strategy where gallic acid solutions containing PCA contamination were added to the culture medium of RB791serA::aroB/pSK6.234, which carried plasmid-localized aroY and utilized the same system for plasmid maintenance as KL7/pSK6.161. It was unlear whether protocatechuate decarboxylase expressed in RB791serA::aroB/pSK6.234 would have access to the gallic acid added to the culture medium although this strategy, from the outset, benefited from the knowledge that stationary phase *E. coli* are more tolerant of catechol's toxicity (Draths, K. M. et al., *J. Am. Chem. Soc.* 117:2395 (1995)). Accordingly, RB791serA::aroB/pSK6.234 was cultured under fermentor conditions to stationary phase. Gallic acid and PCA were added to the culture medium to give conentrations of 115 mM and 4.5 mM, respectively, followed by termination of glucose addition. Airflow was also terminated and the fermentor was sparged with a continuous flow of $N_2$. Within 14 h (FIG. 8), gallic acid and PCA were converted into a solution containing 112 mM pyrogallol (97%) and 4 mM catechol. Repetition of the decarboxylation with culture supernatant produced by KL7/pSK6.161 resulted in a 93% yield of pyrogallol. The concentrations of DHS, DAH, and glutamic acid remained unchanged. Pyrogallol was isolated from cell-free culture supernatants by extraction with EtOAc. Removal of solvent from the charcoal-decolorized organic layer followed by heating under vacuum to remove catechol contamination afforded pyrogallol as a white solid.

II. Materials and Methods

General. For $^1H$ NMR quantitation of solute concentrations, solutions were concentrated to dryness under reduced pressure, concentrated to dryness one additional time from $D_2O$, and then redissolved in $D_2O$ containing a known concentration of the sodium salt of 3-(trimethylsilyl)propionic-2,2,3,3-$d_4$ acid (TSP) purchased from Lancaster Synthesis Inc. Concentrations were determined by comparison of integrals corresponding to each compound with the integral corresponding to TSP ($\delta$=0.00 ppm) in the $^1H$ NMR. All $^1H$ NMR spectra were recorded on a Varian VXR-300 FT-NMR Spectrometer (300 MHz). Glucose concentrations in fermentation broths were measured using the Glucose Diagnostic Kit purchased from Sigma.

Culture Medium. All solutions were prepared in distilled, deionized water. LB medium contained (per L) Bacto tryptone (10 g), Bacto yeast extract (5 g), and NaCl (10 g). M9 salts contained (per L) $Na_2HPO_4$ (6 g), $KH_2PO_4$ (3 g), NaCl (0.5 g) and $NH_4Cl$ (1 g). M9 minimal medium (per L) consisted of 1 L of M9 salts containing D-glucose (10 g), $MgSO_4$ (0.12 g), and thiamine hydrochloride (0.001 g). Aromatic amino acid supplementation consisted of L-phenylalanine (40 mg/L), L-tyrosine (40 mg/L), L-tryptophan (40 mg/L), potassium p-aminobenzoate (10 mg/L), p-hydroxybenzoic acid (10 mg/L), and 2,3-dihydroxybenzoic acid (10 mg/L). Serine (40 mg/L) and shikimic acid (40 mg/L) supplementation were added where necessary. Ampicillin (50 mg/L) and chloramphenicol (20 mg/L) were added where appropriate. Solutions of inorganic salts, D-glucose, and $MgSO_4$ were autoclaved separately. Thiamine, antibiotics, and growth supplements including amino acids and vitamins were sterilized through 0.22-$\mu$m membranes prior to addition to the medium. Solid medium was prepared by addition of 1.5% (w/v) Difco agar to the medium solution.

Fermentation medium (1 L) contained $K_2HPO_4$ (7.5 g), ammonium iron (III) citrate (0.3 g), citric acid monohydrate (2.1 g), L-phenylalanine (0.7 g), L-tyrosine (0.7 g), L-tryptophan (0.35 g), and concentrated $H_2SO_4$ (1.2 mL). Fermentation medium was adjusted to pH 7.0 by addition of concentrated NH$_4$OH before autoclaving. The following supplements were added immediately prior to initiation of the fermentation: D-glucose (23 g or 30 g, as specified), MgSO$_4$ (0.24 g), p-hydroxybenzoic acid (0.010 g), potassium p-aminobenzoate (0.010 g), 2,3-dihydroxybenzoic acid (0.010 g), and trace minerals including (NH$_4$)$_6$(Mo$_7$O$_{24}$).4H$_2$O (0.0037 g), ZnSO$_4$.7H$_2$O (0.0029 g), H$_3$BO$_3$ (0.0247 g), CuSO$_4$.5H2O (0.0025 g), and MnCl$_2$.4H$_2$O (0.0158 g). Inorganic salts containing the aromatic amino acid supplements were autoclaved separately from solutions of D-glucose and MgSO$_4$. Aromatic vitamins and trace minerals were sterilized through 0.22-$\mu$m membranes.

Genetic Manipulations. Standard procedures were used for construction, purification, and analysis of plasmid DNA (Sambrook, J. et al., *Molecular Cloning: A Laboratory Manual;* Cold Spring Harbor Laboratory: Plainview, N.Y. (1990)). *E. coli* DH5$\alpha$ served as the host strain for all plasmid constructions. PCR amplifications were carried out as described by Sambrook (Sambrook, J. et al., *Molecular Cloning: A Laboratory Manual;* Cold Spring Harbor Laboratory: Plainview, N.Y. (1990)). Each reaction (0.1 mL) contained 10 mM KCl, 20 mM Tris-HCl (pH 8.8), 10 mM (NH$_4$)$_2$SO$_4$, 2 mM MgSO$_4$, 0.1% Triton X-100, dATP (0.2 mM), dCTP (0.2 mM), dGTP (0.2 mM), dTTP (0.2 mM), template DNA, 0.5 $\mu$M of each primer, and 2 units of Vent polymerase (New England Biolabs). Initial template concentrations varied from 0.02 to 1 $\mu$g.

Strain Construction. *E. coli* RB791serA::aroB was prepared from RB791 by homologous recombination of the aroB gene into the serA locus. Localization of the serA gene in pMAK705 followed by insertion of aroB into a restriction site internal to serA directed recombination of aroB into the serA locus of the RB791 genome. Digestion of pKAD63 (Snell, K. et al., *J. Am. Chem. Soc.* 118:5605 (1996)) with Sph I liberated a 1.9 kb serA fragment, which was subsequently inserted into the Sph I site of pMAK705 to afford pKAD76A (Snell, K. D. et al., *J. Am. Chem. Soc.* 118:5605 (1996)). The aroB gene was obtained as a 1.7 kb fragment following digestion of pJB14 with EcoR I. Insertion of the aroB fragment into the EcoR I site of serA was complicated by two additional EcoR I sites in pKAD76A. Following partial EcoR I digestion of pKAD76A the resulting DNA fragments were resolved on an agarose gel, and the 7.4 kb fragment corresponding to linearized plasmid was isolated. Ligation of the linearized pKAD76A to the 1.7 kb EcoR I fragment of aroB afforded candidates which were screened for inability to complement the serine auxotrophy of *E. coli* JC158 (Clark, A. J., *Genetics* 48:105 (1963)). Plasmid pKL3.82A was isolated in which aroB was found to be localized in the EcoR I site internal to the serA sequence. Homologous recombination of the serA::aroB locus of pKL3.82A into RB791 followed the procedure described by Hamilton, C. M. et al., *J. Bacteriol.* 171:4617 (1989) and Ohta, K. et al., *Appl. Environ. Microbiol.* 57:893 (1991). *E. coli* RB791 serA::aroB was isolated based on the following growth characteristics on agar plates: no growth on M9, growth on M9 containing serine, no growth on LB containing chloramphenicol, and growth on LB.

pSK6.232. Plasmid pSK6.232 (FIG. 2) is a 12.1 kb pJF118EH-based plasmid (Furste, J. P. et al., *Gene* 48: 119 (1986)) that contains a 1.1 kb aroF$^{FBR}$ ORF transcribed from the vector encoded P$_{tac}$ promoter, a 2.3 kb aroY-encoding insert, a 1.5 kb P$_{tac}$pobA* insert, and a 1.9 kb serA-encoding insert. Strains containing pSK6.232 are resistant to ampicillin. Expression of aroF$^{FBR}$ and pobA* is regulated by IPTG addition, which is mediated by the pJF118EH-encoded lacI$^q$ gene.

pSK6.234. Plasmid pSK6.234 (FIG. 2) is a 6.5 kb pSU18-based vector which contains a 2.3 kb aroY-encoding insert and a 1.9 kb serA-encoding insert. Strains containing pSK6.234 are resistant to chloramphenicol.

Fed-batch Fermentation. Cultures were grown in a 2.0 L capacity Biostat MD B-Braun fermentor connected to a DCU system and a Dell Optiplex Gs+ 5166M personal computer equipped with B-Braun MFCS/win software. The temperature and pH were controlled with a PID controller. Substrate feeding was controlled either manually or via PID controller. The temperature was maintained at 36° C. pH was maintained at 7.0 by addition of concentrated NH$_4$OH or 2 N H$_2$SO$_4$. Dissolved oxygen (D.O.) was measured using a Braun polarographic probe and was set at either 10% or 20% air saturation, as indicated. Antifoam (Sigma 204) was pumped in manually as needed.

RB791serA::aroB/pSK6.234 Fermentation. A single colony of RB791serA::aroB/pSK6.234 was inoculated into 5 mL of LB containing chloramphenicol and supplemented with glucose (4 g/L). Cells were grown overnight at 37° C. with agitation. Cells from 3 mL of the culture were harvested, washed in M9 salts, and used to inoculate 100 mL of M9 minimal medium (500 mL Erlenmeyer flask) containing D-glucose (8 g/L) and chloramphenicol. After growth at 37° C., 250 rpm for 10 h, the inoculant was ready for transfer into the fermentor vessel.

The initial glucose concentration in the fermentation medium was 23 g/L, and the fermentation was run at 36° C. Three staged methods were used to maintain D.O. at 20% of air saturation during the fermentation process. In the first stage, the airflow was set to 0.06 L/L/min and D.O. was maintained by increasing the impeller speed from a preset minimum value of 50 rpm to a preset maximum value of 940 rpm. This stage of the fermentation required approximately 5.5 h. The second stage began after the impeller speed reached its maximum value at which time the mass flow controller maintained D.O. levels at 20% air saturation by increasing the airflow. Approximately 1.5 h were needed for the airflow to increase from 0.06 L/L/min to its preset maximum rate of 1.0 L/L/min. In the third stage, at a constant impeller speed of 940 rpm and a constant airflow of 1.0 L/L/min, D.O. levels were maintained at 20% saturation by oxygen-sensor-controlled glucose (60% w/v) feeding. The PID control parameters were set to 0.0 (off) for the derivative control ($\tau_D$) and 999.9 s (minimum action control) for integral control ($\tau_I$). $X_p$ was set to 950% to achieve a $K_c$ of 0.1. The third stage of control was continued until a gallic acid-containing solution was added to the fermentor broth.

RB791serA::aroB/pSK6.234-catalyzed decarboxylations were performed on two different solutions. In one case, gallic acid monohydrate (149 mmol, 28 g) and protocatechuic acid (5.8 mmol, 0.9 g) were combined in 80 mL of water and the pH was adjusted to 6.5 by addition of concentrated NH$_4$OH. After autoclaving for 7 minutes, the homogeneous solution was ready for addition into the fermentor. In a second case, cell-free fermentor broth (1 L) produced by KL7/pSK6.161 containing gallic acid (118 mM, 20 g/L), protocatechuic acid (4.5 mM, 0.7 g/L), 3-dehydroshikimic acid (23.8 mM, 4.1 g/L), 3-deoxy-D-arabino-heptulosonic acid (32.0 mM, 6.6 g/L), and glutamic acid (102 mM, 15 g/L) was utilized. In each case, gallic acid-containing solution was added in a single portion to a fermentation of RB791serA::aroB/pSK6.234 which had been growing for 24 h past inoculation. Airflow was exchanged for nitrogen flow of 0.5 L/L/min and glucose addition was discontinued. Decarboxylation was followed by $^1$H NMR analysis of cell-free fermentor broth at two hour intervals. Complete decarboxylation of gallic acid was usually observed approximately 14 h after addition of gallic acid-containing solution to the fermentor.

Fermentation broth was harvested by centrifugation at 13000 g for 10 min, and the cells were discarded. Fermentor broth (1 L) containing pyrogallol (49 mM, 6.2 g/L), catechol (3 mM, 0.33 g/L), 3-dehydroshikimic acid (12 mM, 2.0 g/L), 3-deoxy-D-arabino-heptulosonic acid (16 mM, 3.3 g/l), and glutamic acid (51 mM, 7.5 g/L) ) was adjusted to pH 2.3 by addition of concentrated $H_2SO_4$. After centrifugation at 13000 g for 10 min to remove precipitated protein, the solution was adjusted to pH 7 by addition of NaOH and then extracted three times with ethyl acetate (600 mL portions). The combined organic fractions were back extracted with one portion of brine (150 mL). The organic layer was stirred with Darco G-60 activated charcoal (4 g) for 5 min and then filtered through celite. Concentration of the filtrate to dryness yielded an off-white powder (5.9 g, 95% isolated yield) consisting of a 33:1 molar ratio of pyrogallol to catechol. High vacuum sublimation of the material in a Kugelrohr apparatus at 61° C. for 1 h resulted in selective sublimation of the contaminating catechol, yielding pure pyrogallol (5.4 g, 87% isolated yield). $^1$ H NMR ($D_2O$) δ6.75 (dd, J=9 Hz, 1H), 6.55 (d, J=9 Hz, 2H).

SPECIFIC EXAMPLE 5

Biocatalytic Synthesis Of Pyrogallol from Gallic Acid by *Klebsiella oxytoca*

In the gallic acid decarboxylation reactions, cleaner pyrogallol (PGL) product may be expected if the contaminating protocatechuic acid (PCA) was metabolized by *K. oxytoca* M5a1 as a result of this organism's ability to use protocatechuic acid as a sole source of carbon for growth. Protocatechuic acid was always present in the gallic acid (GA) fermentation solutions and resulted in catechol contamination of product pyrogallol.

Initial protocatechuic acid decarboxylations using *K. oxytoca* M5a1 utilized the standard conditions that were previously employed for the *E. coli* biocatalyst (see, Specific Example 4). *K. oxytoca* M5a1 was grown to stationary phase in a fermentor, before addition of a mixture (150 mL) of GA.$H_2O$ (28 g) and PCA (1.5 g). No pyrogallol or catechol was observed after 6 h of reaction and the concentration of gallic acid and protocatechuic acid remained unchanged. Interestingly, protocatechuic acid was not metabolized, even though the glucose feed was terminated prior to addition of the GA/PCA mixture. The fermentation conditions employed for *E. coli*-catalyzed decarboxylations were therefore not appropriate for *K. oxytoca* M5a1.

Figure 9:
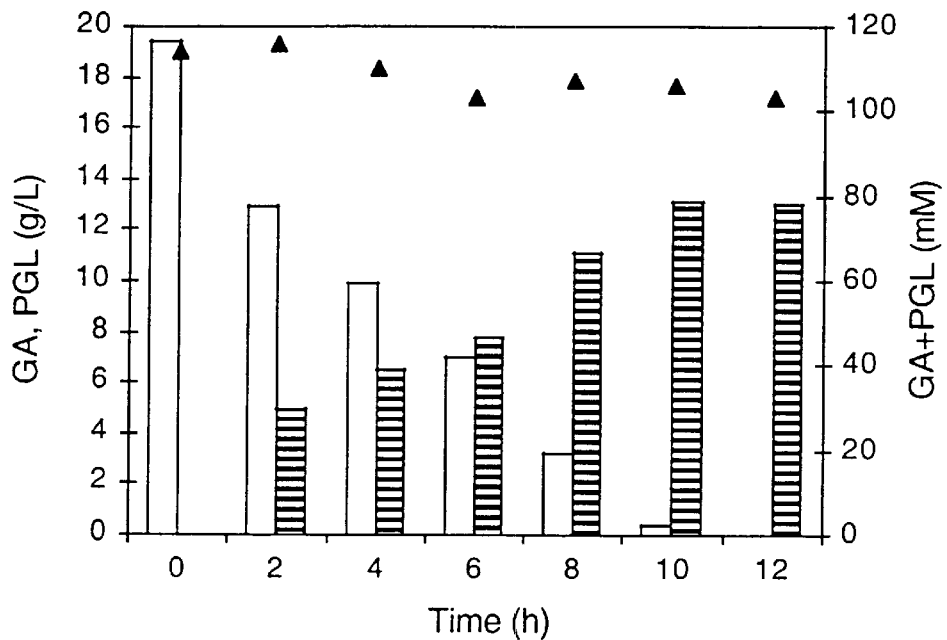
FIG. 9 is a graph showing the conversion of gallic acid to pyrogallol catalyzed by *Klebsiella oxytoca*.

*K. oxytoca* M5a1 cells cultured under fermentor conditions until maximum airflow was reached at 6 h, and then grown for 2 more hours to mid-log phase. The GA/PCA mixture was then added. Glucose addition was continued after GA/PCA addition to maintain an excess of glucose and the airflow was decreased to 0.5 L/L/min. Approximately 2–4 h later, D.O. levels begun to increase and could not be controlled by glucose addition. At this point, airflow was terminated and $N_2$ sparging initiated and maintained at 0.25 L/L/min until the end of the run. In a typical experiment gallic acid (114 mM, 19.4 g/L) and protocatechuic acid (12 mM, 1.8 g/L), were decarboxylated in 12 h to pyrogallol (105 mM, 13.2 g/L) and catechol (10 mM, 1.5 g/L) in 95% (mol/mol) yield (FIG. 9). Purification or pyrogallol from the *K. oxytoca* M5a1 solutions was identical to that as previously described for *E. coli* (see, Specific Example 4).

Under the fermentation conditions employed for gallic acid decarboxylation, an excess of glucose was always present. However, its rate of utilization by the microbe declined as the pyrogallol concentration increased. Growth inhibition was usually observed after 3–4 after addition of the GA/PCA mixture. In experiments where the glucose feed was terminated before decarboxylation was finished (80 mM PGL, 25 mM GA, 160 mM glucose) at 7 h, complete decarboxylation by 14 h was observed without any further glucose consumption. In similar experiments where glucose was consumed by 3 h (50 mM PGL, 62 mM GA) as a result of one time addition, incomplete reaction was observed even after 19 h or reaction time (78 mM PGL, 34 mM GA) when no additional glucose was added. Protocatechuic acid (12 mM) was not metabolized even under these glucose-limited conditions. It appears, that although glucose is not necessarily consumed in large amounts during decarboxylation, its presence is important for completing the reaction. In a typical run, around 70 g of glucose were consumed, a number almost identical to the 72 g that were consumed by *E. coli* for the same reaction.

The decarboxylation reaction was due to an aroY-encoded PCA decarboxylase gene that is native to Klebsiella. The aroY gene, which encodes PCA decarboxylase, was originally isolated from a genomic library of *K. pneumoniae* (Draths, K. M. et al., *J. Am. Chem. Soc.* 119:2395 (1995)). Although this enzyme's primary substrate was protocatechuic acid, complete decarboxylation of gallic acid by recombinant *E. coli* expressing an aroY from a plasmid was achieved. Using partially purified enzyme, the activity of AroY towards the decarboxylation of both gallic acid and protocatechuic acid has been previously established.

The foregoing discussion discloses and describes merely exemplary embodiments of the present invention. One skilled in the art will readily recognize from such discussion, and from the accompanying drawings and claims, that various changes, modifications and variations can be made therein without departing from the spirit and scope of the invention as defined in the following claims.

All references cited herein are incorporated by reference as if fully set forth.

I claim:

1. A method for the production of gallic acid from a carbon source, comprising:
    a) providing a host cell which is capable of converting the carbon source to 3-dehydroshikimic acid and comprising a recombinant DNA encoding an enzyme which converts 3-dehydroshikimic acid to protocatechuic acid and a recombinant DNA encoding an enzyme which converts protocatechuic acid to gallic acid; and
    b) culturing the host cell in the presence of the carbon source.

2. The method of claim 1 wherein the host cell is selected from the species *E. coli*.

3. The method of claim 1 wherein the recombinant DNA encoding an enzyme which converts protocatechuic acid to gallic acid is a recombinant DNA encoding a p-hydroxybenzoate hydroxylase.

4. The method of claim 3 wherein the recombinant DNA encoding a p-hydroxybenzoate hydroxylase is a *Pseudomonas aeruginosa* pobA*.

5. The method of claim 4 wherein the pobA* is in a plasmid.

6. The method of claim 5 wherein the plasmid is pSK6.161.

7. The method of claim 1 wherein the enzyme which converts the 3-dehydroshikimic acid to protocatechuic acid is 3-dehydroshikimate dehydratase.

8. The method of claim 7 wherein the recombinant DNA encoding the 3-dehydroshikimate dehydratase is aroZ.

9. The method of claim 8, wherein the aroZ is in a serA locus of the host cell.

10. The method of claim 1 wherein the host cell further comprises a recombinant DNA molecule encoding an isozyme of 3-deoxy-D-arabino-heptulosonate-7-phosphate synthase insensitive to feedback inhibition by aromatic amino acids or other aromatic molecules.

11. The method of claim 10 wherein the recombinant DNA molecule encoding an isozyme of 3-deoxy-D-arabino-heptulosonate-7-phosphate synthase is aroF$^{FBR}$.

12. The method of claim 11 wherein the aroF$^{FBR}$ is in a plasmid.

13. The method of claim 12 wherein the plasmid is pSK6.161.

14. The method of claim 3 wherein the host cell further comprises a lacI$^q$ gene encoding a lac repressor.

15. The method of claim 14 wherein the lacI$^q$ is in a plasmid.

16. The method of claim 15 wherein the plasmid is pSK6.161.

17. The method of claim 14 wherein the expression of p-hydroxybenzoate hydroxylase is repressed when culturing the host cell until late-log phase or stationary phase.

18. A method for producing gallic acid from a carbon source comprising culturing, in the presence of the carbon source, a cell which has been transformed by introducing into the cell (a) a recombinant DNA encoding an enzyme which converts 3-dehydroshikimic acid to protocatechuic acid and (b) a recombinant DNA encoding an enzyme which converts protocatechuic acid to gallic acid.

19. A method for the production of gallic acid from a carbon source comprising converting the carbon source to gallic acid with a recombinant *E. coli* comprising the genes encoding an isozyme of 3-deoxy-D-arabino-heptulosonate-7-phosphate synthase insensitive to feedback inhibition by aromatic amino acids or other aromatic molecules, a 3-dehydroquinate synthase, a 3-dehydroshikimate dehydratase, and a mutant p-hydroxybenzoate hydroxylase capable of catalyzing the hydroxylation of protocatechuic acid to gallic acid.

20. The method of claim 19 wherein the recombinant *E. coli* comprises:

a) an aroZ cassette inserted into a serA locus; and b) a plasmid comprising $P_{tac}$pobA*, lacI$^q$, aroF$^{FBR}$, and serA inserts.

21. The method of claim 20 wherein the plasmid is pSK6.161.

22. The method of claim 19 wherein the recombinant *E. coli* is *E. coli* KL7/pSK6.161.

* * * * *

UNITED STATES PATENT AND TRADEMARK OFFICE
CERTIFICATE OF CORRECTION

PATENT NO. : 6,472,190 B1
DATED : October 29, 2002
INVENTOR(S) : John W. Frost

It is certified that error appears in the above-identified patent and that said Letters Patent is hereby corrected as shown below:

Title page,
Item [56], References Cited, OTHER PUBLICATIONS, "Li K. et al." reference, "Rcombinant" should be -- Recombinant --.

Column 5,
Line 46, "$Pt_{tac}pobA*$" should be -- $P_{tac}pobA*$ --.

Column 6,
Line 2, "sera" should be -- serA --.
Line 50, "3-dehydroshikmic" should be -- 3-dehydroshikimic --.

Column 7,
Line 20, "aroy-encoded" should be -- aroY-encoded --.

Column 9,
Line 63, "andpobA*" should be -- and pobA * --.

Column 11,
Line 4, "$NH_4OH$" should be -- $NH_4OH$ --.
Line 18, "*Cloning.*" should be -- *Cloning*: --.

Column 15,
Line 1, "MgSO4" should be -- $MgSO_4$ --.
Line 13, "$(NH_4)2SO_4$" should be -- $(NH_4)_2SO_4$ --.
Line 20, "sera" should be -- serA --.

Column 16,
Line 15, "pE130" should be -- pIE130 --.
Line 46, "360° C." should be -- 36° C. --.

Column 20,
Line 65, "Let" should be -- set --.

UNITED STATES PATENT AND TRADEMARK OFFICE
CERTIFICATE OF CORRECTION

PATENT NO. : 6,472,190 B1
DATED : October 29, 2002
INVENTOR(S) : John W. Frost

It is certified that error appears in the above-identified patent and that said Letters Patent is hereby corrected as shown below:

Column 21,
L:ine 37, "PTA" should be -- PCA --

Column 22,
Line 4, "unlear" should be -- unclear --.
Line 13, "conentrations" should be -- concentrations --.

Column 23,
Line 8, "5H20" should be -- $5H_2O$ --.

Column 25,
Line 9, "g/l" should be -- g/L --.

Signed and Sealed this

Twenty-fourth Day of August, 2004

JON W. DUDAS
*Director of the United States Patent and Trademark Office*

UNITED STATES PATENT AND TRADEMARK OFFICE
CERTIFICATE OF CORRECTION

PATENT NO. : 6,472,190 B1
DATED : October 29, 2002
INVENTOR(S) : John W. Frost

It is certified that error appears in the above-identified patent and that said Letters Patent is hereby corrected as shown below:

Column 3,
Line 51, "dehydrogenase" should be -- dehydratase --.

Signed and Sealed this

Ninth Day of August, 2005

JON W. DUDAS
*Director of the United States Patent and Trademark Office*

UNITED STATES PATENT AND TRADEMARK OFFICE
CERTIFICATE OF CORRECTION

| | | |
|---|---|---|
| PATENT NO. | : 6,472,190 B1 | Page 1 of 1 |
| APPLICATION NO. | : 09/527145 | |
| DATED | : October 29, 2002 | |
| INVENTOR(S) | : John W. Frost | |

It is certified that error appears in the above-identified patent and that said Letters Patent is hereby corrected as shown below:

In the Specification

Column 1, Line 4, delete – "SPONSORHIP – Work on this invention was sponsored in part by the National Science Foundation Grant No. CHE9633368 and the Environmental Protection Agency Grant No. CR822940. The Government may have certain rights inthe invention." and insert therefor –

--GOVERNMENT SUPPORT CLAUSE

This invention was made with government support under CHE9633368 awarded by the National Science Foundation and CR822940 awarded by the Environmental Protection Agency. The government has certain rights in the invention.--

Signed and Sealed this
Eighth Day of April, 2014

Michelle K. Lee
*Deputy Director of the United States Patent and Trademark Office*